(12) United States Patent
Niitsu

(10) Patent No.: US 9,572,886 B2
(45) Date of Patent: Feb. 21, 2017

(54) AGENT FOR TREATING MYELOFIBROSIS

(71) Applicant: Nitto Denko Corporation, Osaka (JP)

(72) Inventor: Yoshiro Niitsu, Sapporo (JP)

(73) Assignee: Nitto Denko Corporation, Osaka (JP)

( * ) Notice: Subject to any disclaimer, the term of this patent is extended or adjusted under 35 U.S.C. 154(b) by 432 days.

(21) Appl. No.: 13/921,049

(22) Filed: Jun. 18, 2013

(65) Prior Publication Data

US 2013/0267581 A1 Oct. 10, 2013

Related U.S. Application Data

(63) Continuation-in-part of application No. 13/648,578, filed on Oct. 10, 2012, now abandoned, which is a continuation of application No. 13/062,214, filed as application No. PCT/JP2009/004369 on Sep. 4, 2009, now abandoned, application No. 13/921,049, which is a continuation-in-part of application No. 13/439,330, filed on Apr. 4, 2012, now Pat. No. 8,652,526, which is a continuation of application No. 11/793,736, filed as application No. PCT/JP2005/023619 on Dec. 22, 2005, now Pat. No. 8,173,170.

(30) Foreign Application Priority Data

Sep. 5, 2008 (JP) ................................. 2008-228338

(51) Int. Cl.
| | |
|---|---|
| *A61K 47/10* | (2006.01) |
| *C12N 15/113* | (2010.01) |
| *A61K 45/06* | (2006.01) |
| *A61K 9/127* | (2006.01) |
| *A61K 47/48* | (2006.01) |
| *A61K 31/07* | (2006.01) |
| *A61K 31/7105* | (2006.01) |
| *C12N 15/11* | (2006.01) |

(52) U.S. Cl.
CPC ............ *A61K 47/10* (2013.01); *A61K 9/1272* (2013.01); *A61K 31/07* (2013.01); *A61K 31/7105* (2013.01); *A61K 45/06* (2013.01); *A61K 47/48107* (2013.01); *A61K 47/48815* (2013.01); *C12N 15/111* (2013.01); *C12N 15/113* (2013.01); *C12N 2310/14* (2013.01); *C12N 2320/32* (2013.01)

(58) Field of Classification Search
CPC .................................................. A61K 31/7088
See application file for complete search history.

(56) References Cited

U.S. PATENT DOCUMENTS

| | | | |
|---|---|---|---|
| 4,966,773 A | 10/1990 | Gressel et al. | |
| 5,472,954 A | 12/1995 | Loftsson | |
| 5,534,261 A * | 7/1996 | Rodgers ............... | A61K 31/203 424/422 |
| 5,583,020 A | 12/1996 | Sullivan | |
| 5,643,584 A | 7/1997 | Farng et al. | |
| 5,668,117 A | 9/1997 | Shapiro | |
| 5,733,572 A | 3/1998 | Unger et al. | |
| 5,753,261 A | 5/1998 | Fernandez et al. | |
| 5,776,915 A * | 7/1998 | Peterson ............... | A61K 9/1272 424/450 |
| 5,785,976 A | 7/1998 | Westesen et al. | |
| 5,811,119 A | 9/1998 | Mehta et al. | |
| 5,820,879 A | 10/1998 | Fernandez et al. | |
| 5,851,538 A | 12/1998 | Froix et al. | |
| 5,942,230 A | 8/1999 | Wu et al. | |
| 6,037,481 A | 3/2000 | Zucchetti et al. | |
| 6,071,495 A | 6/2000 | Unger et al. | |
| 6,159,591 A | 12/2000 | Beihoffer et al. | |
| 6,177,274 B1 | 1/2001 | Park et al. | |
| 6,183,774 B1 | 2/2001 | Aust et al. | |
| 6,187,315 B1 | 2/2001 | Falcon | |
| 6,214,345 B1 | 4/2001 | Firestone et al. | |
| 6,217,912 B1 | 4/2001 | Park et al. | |
| 6,238,917 B1 | 5/2001 | Hendry et al. | |
| 6,248,363 B1 | 6/2001 | Patel et al. | |
| 6,251,428 B1 | 6/2001 | Yoo | |
| 6,328,988 B1 | 12/2001 | Uhrich | |
| 6,342,219 B1 | 1/2002 | Thorpe | |
| 6,342,221 B1 | 1/2002 | Thorpe et al. | |
| 6,344,206 B1 | 2/2002 | Nguyen et al. | |
| 6,379,683 B1 | 4/2002 | Simonnet et al. | |
| 6,441,025 B2 | 8/2002 | Li et al. | |
| 6,471,968 B1 | 10/2002 | Baker, Jr. et al. | |

(Continued)

FOREIGN PATENT DOCUMENTS

| | | |
|---|---|---|
| CA | 2595517 | 6/2006 |
| CN | 101102795 A | 1/2008 |
| EP | 0932399 | 8/1999 |
| EP | 1842557 | 10/2007 |
| EP | 1842557 A1 * | 10/2007 |
| EP | 2135600 | 12/2009 |
| EP | 2258395 | 12/2010 |
| JP | H02-502094 | 7/1990 |
| JP | B 8-002799 | 1/1996 |
| JP | H 082799 B2 | 1/1996 |

(Continued)

OTHER PUBLICATIONS

Fourth Office Action dated Jul. 28, 2014 for Chinese Application No. 201110316481.3, filed Dec. 22, 2005.

(Continued)

*Primary Examiner* — Gollamudi Kishore
*Assistant Examiner* — Amanda Heyes
(74) *Attorney, Agent, or Firm* — Knobbe Martens Olson & Bear LLP

(57) ABSTRACT

Disclosed is a substance delivery carrier for an extracellular-matrix-producing cell in the bone marrow, which comprises a retinoid. Also disclosed in an agent for treating myelofibrosis by utilizing a substance capable of regulating the activity or proliferation of an extracellular-matrix-producing cell in the bone marrow.

3 Claims, 8 Drawing Sheets

(56) References Cited

U.S. PATENT DOCUMENTS

| | | |
|---|---|---|
| 6,472,507 B1 | 10/2002 | Fischer et al. |
| 6,524,583 B1 | 2/2003 | Thorpe et al. |
| 6,586,524 B2 | 7/2003 | Sagara |
| 6,610,841 B1 | 8/2003 | Warren |
| 6,645,528 B1 | 11/2003 | Straub et al. |
| 6,652,886 B2 | 11/2003 | Ahn et al. |
| 6,656,734 B1 | 12/2003 | Bischoff et al. |
| 6,676,941 B2 | 1/2004 | Thorpe et al. |
| 6,680,047 B2 | 1/2004 | Klaveness et al. |
| 6,696,038 B1 | 2/2004 | Mahato et al. |
| 6,730,334 B2 | 5/2004 | Zhao |
| 6,740,336 B2 | 5/2004 | Trubetskoy et al. |
| 6,746,678 B1 | 6/2004 | Shapiro |
| 6,764,698 B1 | 7/2004 | Byun et al. |
| 6,838,528 B2 | 1/2005 | Zhao |
| 6,896,890 B2 | 5/2005 | Singh et al. |
| 6,908,626 B2 | 6/2005 | Cooper et al. |
| 6,994,862 B2 | 2/2006 | Jeong et al. |
| 6,998,115 B2 | 2/2006 | Langer et al. |
| 7,018,655 B2 | 3/2006 | Lele et al. |
| 7,045,356 B2 | 5/2006 | Trubetskoy et al. |
| 7,060,498 B1 | 6/2006 | Wang |
| 7,064,127 B2 | 6/2006 | Friedman et al. |
| 7,071,163 B2 | 7/2006 | Sokoloff et al. |
| 7,074,389 B2 | 7/2006 | Frankenberger et al. |
| 7,098,030 B2 | 8/2006 | Rozema et al. |
| 7,101,576 B2 | 9/2006 | Hovey et al. |
| 7,101,995 B2 | 9/2006 | Lewis et al. |
| 7,122,202 B2 | 10/2006 | Allen et al. |
| 7,196,145 B2 | 3/2007 | Ignacious |
| 7,223,724 B1 | 5/2007 | Alderson et al. |
| 7,223,837 B2 | 5/2007 | De Groot et al. |
| 7,259,011 B2 | 8/2007 | Lucas et al. |
| 7,262,221 B2 | 8/2007 | Uhrich et al. |
| 7,265,186 B2 | 9/2007 | Zhao |
| 7,276,249 B2 | 10/2007 | Ryde et al. |
| 7,276,348 B2 | 10/2007 | Glick |
| 7,297,515 B1 | 11/2007 | Szankasi et al. |
| 7,297,786 B2 | 11/2007 | McCray et al. |
| 7,316,811 B2 | 1/2008 | Zhao et al. |
| 7,320,802 B2 | 1/2008 | Ryde et al. |
| 7,358,223 B2 | 4/2008 | Zhao et al. |
| 7,404,969 B2 | 7/2008 | Chen et al. |
| 7,700,541 B2 | 4/2010 | Tanaka et al. |
| 7,700,542 B2 | 4/2010 | Zhao et al. |
| 8,003,621 B2 | 8/2011 | Niitsu et al. |
| 8,173,170 B2 | 5/2012 | Niitsu et al. |
| 8,178,124 B2 | 5/2012 | Niitsu et al. |
| 8,258,235 B2 | 9/2012 | Zhao et al. |
| 8,574,623 B2 | 11/2013 | Niitsu et al. |
| 8,652,526 B2 | 2/2014 | Niitsu et al. |
| 8,686,052 B2 | 4/2014 | Niitsu et al. |
| 2002/0012998 A1 | 1/2002 | Gonda et al. |
| 2002/0026060 A1 | 2/2002 | Belloni et al. |
| 2002/0041898 A1* | 4/2002 | Unger ............... A61K 9/1075 424/486 |
| 2002/0048798 A1 | 4/2002 | Avery et al. |
| 2002/0143062 A1 | 10/2002 | Lopez-Berestein et al. |
| 2003/0064094 A1 | 4/2003 | Frankenberger et al. |
| 2003/0073619 A1 | 4/2003 | Mahato et al. |
| 2003/0096739 A1 | 5/2003 | Morris |
| 2003/0147958 A1 | 8/2003 | Ahn et al. |
| 2003/0161791 A1* | 8/2003 | Bentley ............. A61K 9/0075 424/46 |
| 2003/0211143 A1 | 11/2003 | Liu et al. |
| 2003/0215395 A1 | 11/2003 | Yu et al. |
| 2004/0028682 A1 | 2/2004 | Border et al. |
| 2004/0071654 A1 | 4/2004 | Anderson et al. |
| 2004/0106125 A1 | 6/2004 | Duggan et al. |
| 2004/0138154 A1 | 7/2004 | Yu et al. |
| 2004/0142474 A1 | 7/2004 | Mahato et al. |
| 2005/0004064 A1 | 1/2005 | Tei et al. |
| 2005/0153337 A1 | 7/2005 | Manoharan |
| 2005/0165227 A1 | 7/2005 | Vlahov et al. |
| 2005/0220859 A1 | 10/2005 | Frankenberger et al. |
| 2005/0256051 A1 | 11/2005 | Morris |
| 2005/0265961 A1 | 12/2005 | Langer et al. |
| 2006/0013775 A1 | 1/2006 | Gristwood et al. |
| 2006/0074041 A1 | 4/2006 | Johnston et al. |
| 2006/0093674 A1 | 5/2006 | Slobodkin et al. |
| 2006/0127482 A1 | 6/2006 | Fewell et al. |
| 2006/0147376 A1 | 7/2006 | Yu et al. |
| 2006/0258751 A1 | 11/2006 | Zhao et al. |
| 2007/0020761 A1 | 1/2007 | Yu et al. |
| 2007/0072171 A1 | 3/2007 | Yu et al. |
| 2007/0243157 A1 | 10/2007 | Tanaka et al. |
| 2008/0014253 A1 | 1/2008 | Jorgensen et al. |
| 2008/0057030 A1 | 3/2008 | Crager |
| 2008/0068227 A1 | 3/2008 | Ogasawara |
| 2008/0131499 A1 | 6/2008 | Leigh et al. |
| 2008/0145338 A1 | 6/2008 | Anderson et al. |
| 2008/0193512 A1 | 8/2008 | Niitsu et al. |
| 2008/0207553 A1 | 8/2008 | Zhao et al. |
| 2008/0220056 A1 | 9/2008 | Arthur et al. |
| 2008/0279765 A1 | 11/2008 | Chettibi et al. |
| 2008/0312174 A1 | 12/2008 | Yu et al. |
| 2009/0105179 A1 | 4/2009 | Yu et al. |
| 2010/0028416 A1* | 2/2010 | Yu et al. ............... 424/450 |
| 2010/0144659 A1 | 6/2010 | Niitsu et al. |
| 2010/0210715 A1 | 8/2010 | Zhao et al. |
| 2011/0104255 A1 | 5/2011 | Niitsu et al. |
| 2011/0178157 A1 | 7/2011 | Jin et al. |
| 2011/0229558 A1 | 9/2011 | Niitsu et al. |
| 2011/0257249 A1 | 10/2011 | Niitsu et al. |
| 2012/0189691 A1 | 7/2012 | Niitsu |
| 2012/0269886 A1 | 10/2012 | Niitsu |
| 2012/0328694 A1 | 12/2012 | Niitsu et al. |
| 2013/0011336 A1 | 1/2013 | Niitsu et al. |
| 2013/0045272 A1 | 2/2013 | Niitsu et al. |
| 2013/0136789 A1 | 5/2013 | Niitsu et al. |
| 2013/0171127 A1 | 7/2013 | Niitsu et al. |
| 2013/0171240 A1 | 7/2013 | Niitsu et al. |
| 2013/0172401 A1 | 7/2013 | Niitsu et al. |
| 2013/0210744 A1 | 8/2013 | Niitsu et al. |
| 2013/0216611 A1 | 8/2013 | Niitsu et al. |
| 2013/0267581 A1 | 10/2013 | Niitsu et al. |
| 2014/0127187 A1 | 5/2014 | Niitsu et al. |
| 2014/0315975 A1 | 10/2014 | Niitsu et al. |
| 2014/0323550 A1 | 10/2014 | Ayabe et al. |

FOREIGN PATENT DOCUMENTS

| | | |
|---|---|---|
| JP | 8-268906 A1 | 10/1996 |
| JP | 11-243968 | 9/1999 |
| JP | 11243968 A * | 9/1999 |
| JP | 11-269076 | 10/1999 |
| JP | 2002-047211 | 2/2002 |
| JP | 2002-47211 | 2/2002 |
| JP | 2002047211 A * | 2/2002 |
| JP | 2002-363094 | 12/2002 |
| JP | 2002-371006 | 12/2002 |
| JP | 2003-119138 | 4/2003 |
| JP | 2003-219893 | 8/2003 |
| JP | 2003-528055 A | 9/2003 |
| JP | 2003-528131 | 9/2003 |
| JP | 2004-083436 A | 3/2004 |
| JP | 2004-523236 | 8/2004 |
| JP | 2004-523236 A | 8/2004 |
| JP | 2004-524371 A | 8/2004 |
| JP | 2005-531564 | 10/2005 |
| JP | 2005-531628 A1 | 10/2005 |
| JP | 2006-506071 | 2/2006 |
| JP | 2007-077116 | 3/2007 |
| JP | 4533420 | 6/2010 |
| JP | 5172880 | 1/2013 |
| WO | WO 88/06883 | 9/1988 |
| WO | WO 91/04748 | 4/1991 |
| WO | WO 97/18842 | 5/1997 |
| WO | WO 97/33618 | 9/1997 |
| WO | WO 00/64478 | 11/2000 |
| WO | WO 01/68081 A1 | 9/2001 |
| WO | WO 01/72283 | 10/2001 |
| WO | WO 02/066646 | 8/2002 |
| WO | WO 02/083186 A1 | 10/2002 |

(56) References Cited

FOREIGN PATENT DOCUMENTS

| WO | WO 02/092600 | 11/2002 |
|---|---|---|
| WO | WO 03/009881 | 2/2003 |
| WO | WO 03/045383 | 6/2003 |
| WO | WO 03/080594 A1 | 10/2003 |
| WO | WO 03/097107 | 11/2003 |
| WO | WO 03/097647 | 11/2003 |
| WO | WO 2004/001381 | 12/2003 |
| WO | WO 2004/002489 A1 | 1/2004 |
| WO | WO 2004/019921 | 3/2004 |
| WO | WO 2004/043239 A2 | 5/2004 |
| WO | WO 2004/065636 | 8/2004 |
| WO | WO 2004/069159 | 8/2004 |
| WO | WO 2004/090108 | 10/2004 |
| WO | WO 2005/032572 | 4/2005 |
| WO | WO 2005/082402 | 9/2005 |
| WO | WO 2006/041617 | 4/2006 |
| WO | WO 2006/066001 | 6/2006 |
| WO | WO 2006/068232 | 6/2006 |
| WO | WO 2006/068232 A1 | 6/2006 |
| WO | WO 2007/067417 | 6/2007 |
| WO | WO 2007/104946 A2 | 9/2007 |
| WO | WO 2007/120479 | 10/2007 |
| WO | WO 2008/006583 A1 | 1/2008 |
| WO | WO 2008/120815 | 10/2008 |
| WO | WO 2008/151150 | 12/2008 |
| WO | WO 2009/036368 | 3/2009 |
| WO | WO 2009/116257 | 9/2009 |
| WO | WO 2010/014117 | 2/2010 |
| WO | WO 2010/026766 | 3/2010 |
| WO | WO 2010/029760 | 3/2010 |

OTHER PUBLICATIONS

Office Action dated Dec. 22, 2014 for Canadian Application No. 2,820,728, filed Dec. 22, 2005.
Communication dated Jan. 21, 2014 in European Application No. 09811296.4 filed on Sep. 4, 2009.
Office Action dated Jan. 15, 2014 for Chinese Application No. 201110316481.3, filed Dec. 22, 2005.
Office Action dated Jun. 9, 2015 for Canadian Application No. 2,735,709, filed Sep. 3, 2009.
Examination Report dated Dec. 25, 2013 for Taiwanese Patent Application No. 098129737, filed on Sep. 3, 2009.
Extended European Search Report dated Jun. 23, 2014 for EP Application No. 13193438.2, filed Dec. 22, 2005.
Extended European Search Report dated Jun. 23, 2014 for EP Application No. 13189691.2, filed Dec. 22, 2005.
Office Action dated Jul. 9, 2013 for Taiwanese Patent application No. 098129737, filed on Sep. 3, 2009.
Examination Report dated Nov. 15, 2013 for Australian Patent Application No. 2009287924, filed on Sep. 4, 2009.
Notification of Reasons for Refusal mailed Feb. 26, 2013 for Japanese Application No. 2008-228338, filed Sep. 5, 2008.
Office Action dated Aug. 22, 2014 for Russian Application No. 2011112645/15(018684), filed on Sep. 4, 2009.
Lowell et al., "Primary and Secondary Myelofibrosis (A Clinical and Pathological Study of Thirteen Cases of Fibrosis of the Bone Marrow)" .Ann. Intern. Med. (1944) 21(5):863-889.
Office Action dated Apr. 12, 2013 in Russian Application No. 2011112645/15(018684), filed Sep. 4, 2009.
Office Action dated May 24, 2013 in Chinese Application No. 200980134538.9, filed Sep. 4, 2009.
Office Action dated Feb. 13, 2015 for Taiwanese Application No. 098129737, filed Sep. 3, 2009.
Lepreux et al., Cellular retinol-binding protein-1 expression in normal and fibrotic/cirrhotic human liver: different patterns of expression in hepatic stellate cells and (myo)fibroblast subpopulations. Journal of Hepatology (2004) 40 (5):774-80.
Moise et al., "Delivery of Retinoid-Based Therapies to Target Tissues" Biochemistry (2007) 46(15):4449-4458.
Kisseleva T. et al., "Fibrogenesis of Parenchymal Organ". Proc Am Thorac Soc. (2008) 5(3):338-42.
Hinz B. et al., "The Myofibroblast: One Function, Multiple Origins" The American Journal of Pathology (2007) 170(6):1807-16.
Office Action dated Apr. 2, 2015 for Japanese Application No. 2014-087058, filed Sep. 3, 2009.
Andrew, E.R., et al., "Molecular motion in solid all-trans retinoic acid (vitamin A acid) by proton NMR." Solid State Nuclear Magnetic Resonance 13, pp. 39-43, 1998.
Dunham et al., Membrane fusion: Studies with a calcium-sensitive dye, arsenazo III, in liposomes. Proceedings of the National Academy of Science, USA, vol. 74, No. 4, pp. 1580-1584, 1997.
Friedman, S. L., "Targeting siRNA to arrest fibrosis," Nature Biotechnology (Apr. 2008) 26(4): 399-400.
Goodman et al., "Extraction and Recombination Studies of the Interaction of Retinol with Human Plasma Retinol-Binding Protein." Journal of Lipid Research, vol. 13, 1972, pp. 338-347.
Hoffman et al, "Biology and Treatment of Primary Myelofibrosis", Hematology Am Soc Hematol Educ Program 2007 2007; 346-54.
Kakumitsu et al, "Transgenic mice overexpressing murine thrombopoietin develop myelofibrosis and osteoclerosis" Leukemia Research 29; 761-769, 2005.
Li, D. et al., "Liver fibrogenesis and the role of hepatic stellate cells: New insights and prospects for therapy," Journal of Gastroenterology and Hepatology 1999; 14(7):618-633.
Leibecq, "Biochemical Nomenclature and Related Documents," $2^{nd}$ Ed. Portland Press, (1992); 247-251.
Shimoda, "Physiopathology and treatment of primary myelofibrosis," The Journal of the Japanese Society of Internal Medicine, (2007); 1398-1404.
Torchilin, V. P. "Drug Targeting," European Journal of Pharmaceutical Sciences. (2000) 11(2):81-91.
Tsuji, H. et al., "Targeting of liposomes surface-modified with glycyrrhizin to the liver. I. Preparation and biological disposition," Chemical & Pharmaceutical Bulletin 1991; 39(4):1004-08.
Vogel et al., "An immortalized rat liver stellate cell line (HSC-TS): a new cell model for the study of retinoid metabolism in vitro." Journal of Lipid Research, vol. 41, 2000, pp. 882-893.
Zhao et al.; "Tumor-selective targeted delivery of genes and antisense oligodeoxyribonucleotides via the folate receptor," Advanced Drug Delivery Reviews (2004) 56: 1193-1204.
Decision of Rejection dated Jul. 31, 2015 for Chinese Application No. 201110316481.3, filed Dec. 22, 2005.
Office Action dated Jan. 13, 2016 for Korean Patent Application No. 10-2011-7005447.
Office Action dated May 9, 2016 for Japanese Application No. 2015-111038.
Extended European Search Report in European application No. 16155975.2-1401, dated Jun. 30, 2016.
Fukuno et al. "A Variant Form of Acute Promyelocytic Leukemia with Marked Myelofibrosis," International Journal of Hematology, vol. 74, No. 3, Oct. 1, 2001, pp. 322-326.
Dutta et al., "Acute promyelocytic leukemia with secondary myelofibrosis—Case report and review of the literature," American Journal of Hematology, vol. 81, No. 6, Jun. 1, 2006, pp. 476-477.
Notification of Reexamination received in Japanese Patent Application No. 201110316481.3, dated Nov. 14, 2016.
Chansri et al., "Inhibition of liver metastasis by all-trans retinoic acid incorporated into O/W emulsions in mice," International Journal of Pharmaceutics 321 (2006) 42-49.
Dunham et al., "Membrane fusion: Studies with a calcium-sensitive dye, arsenazo III, in lipsomes," Proc. Natl, Acad. Sci., vol. 74. No. 4, pp. 1580-1584, Apr. 1977.
Ermak et al., "Monoclonal antibody-directed targeting of fluorescent polystyrene microspheres to Peyer's patch M cells,".
Fortunati et al., "A multi-domain protein for $\beta_1$ integrin-targeted DNA delivery," Gene Therapy (2007) 7, 1505-1515.
Hoffman, et al., "Biology and Treatment of Primary Myelofibrosis,"Am. Soc. Of Hematology, (2007): 346-354.
Hwang et al., "Phospholipid-based microemulsion formulation of all-trans-retinoic acid for parenteral administration," International Journal of Pharmaceutics 276 (2004) 175-183.

(56) References Cited

OTHER PUBLICATIONS

International Search Report dated Oct. 20, 2009 for International Application No. PCT/JP2009/004369, filed Sep. 4, 2009.
Kim et al., "Folate-tethered emulsion for the target delivery of retinoids to cancer cells," European Journal of Pharmaceuticals and Biopharmaceutics 68 (2008) 618-625.
Kircheis et al., "Tumor targeting with surface-shielded ligand-polycation DNA compleses," Journal of Controlled Release 72 (2001) 165-170.
Li et al., "Transferrin/Transferrin Receptor-Mediated Drug Delivery," Medical Research Reviews, vol. 22, No. 3, 225-250, 2002.
Liébecq, "Biochemical Nomenclature and Related Documents,"*2nd Ed. Portland Press*, (1992): 247-251.
Lim et al., "Formulation parameters determining the physicochemical characteristics of solid lipid nanoparticles loaded with all-trans retinoic acid," International Journal of Pharmacuetics 243 (2002) 135-146.
Ma et al., "Comparison of Stability for All-*trans* Retinoic Acid Nanosuspensions and Lipid Nanoparticle Formulations," IEEE/ICME International Conference on Complex Medical Engineering, pp. 197-202, 2007.
Marcucci et al., "Active targeting with particulate drug carriers in tumor theraph: fundamentals and recent progress," Drug Discovery Today vol. 9, No. 5, Mar. 2004 pp. 219-228.
Noa Noy, "Retinoid-biding proteins: Mediators of retinoid action," Biochem J. (2000) 248. 481-495.
Sato et al., "Resolution of liver cirrhosis using vitamin A-Couple liposomes to deliver siRNA against a collagen-specific chaperone," Nature Biotechnology, vol. 26, No. 4, Apr. 2008.
Scott L. Friedman, "Targeting siRNA to arrest fibrosis," Nature Biotechnology vol. 26, No. 4, Apr. 2008.
Shimoda, "Physiopathology and treatment of primary myelofibrosis,"*The Journal of the Japanese Society of Internal Medicine*, (2007) 96(7):1398-1404.
Torchilin et al., "Imminomicelles: Targeted pharmaceutical carriers for poorly soluble drugs," PNAS, May 13, 2003, Vo. 100, No. 10, pp. 6039-6044.
Viguera et al., "A Water-soluable Polylysine-Retinaldehyde Schiff Base," The Journal of Biological Chemistry, vol. 265, No. 5, Issue of Feb. 15, pp. 2527-2532, 1990.
Vladimir P. Torchilin, "Drug Targeting," European Journal of Pharmaceutical Sciences 11 Suppl. 2 (2000) S81-S91.
Watanabe, et al., "Treatment of Idiopathic Myelofibrosis Employing siRNA for Heat Shock Protein 47 (siRNA/HSP47) Encapsulated in Liposomes,"*Blood*, (2007) 110(11):235(B).
Whitmer et al, "Membrane-membrane interactions associated with rapid transfer of liposomal bilirubin to microsomal UDP-glucuronyltransferase," Biochem. J. (1987) 244, 41-47.
Winter et al., "Molecular Imaging of Angiogenesis in Nascent Vx-2 Rabbit Tumors Using a Novel □ □₃-targeted Nanoparticle and 1.5 Tesla Magnetic Resonance Imaging," Cancer Res 2003; 63:5838-5843, Published on line Oct. 1, 2003.
Office Action dated Feb. 26, 2013 for Japanese Application No. 2008-228338, filed on Sep. 5, 2008.
Brash, E. D. and Havre, P. A., "New careers for antioxidants,"*Proceedings of the National Academy of Sciences*, (Oct. 2002) 99(22): 13969-13971.
Saito, M. et al., "Cytotoxicity and apoptosis induction by butylated hydroxyanisole (BHA) and butylated hydroxytoluene (BHT),"*Anticancer Res*. (2003) 23(6C): 4693-4701.
Sakagami, H. et al., "Apoptpsis-inducing activity of vitamin C and vitamin K,"*Cell Mol. Biol (Noisy-le-grand)* (Feb. 2000) 46(1): 129-143.
Sigounas, G. et al., "dl-alpha-Tocopherol induces apoptosis in erythroleukemia, prostate, and breast cancer cells,"*Nutrition and Cancer*, (1997) 28(1): 30-35.
Szondy, Z. et al., "Induction of apoptosis by retinoids and retinoic acid receptorg-selective compounds in mouse thymocytes through a novel apoptosis pathway,"*Molecular Pharmacology* (1997) 51: 972-982.

Kim et al., "Retinol-encapsulated low molecular water-soluble chitosan nanoparticles" International Journal of Pharmaceutics,(2006) 319(1-2):130-138.
Jeong et al., "Polyion complex micelles composed of all-trans retinoic acid and poly (ethylene glycol)-grafted-chitosan" Journal of Pharmaceutical Sciences (2006) 95(11):2348-2360.
Extended Search Report dated Oct. 2, 2012, issued in European Patent Application No. 09811296.4, filed on Sep. 4, 2009.
Agrawal, et al., "Antisense therapeutics: Is it as simple as complimentary base recognition?"*Molecular Med. Today* (2000) 6: 72-81.
Beljaars, et al., "Albumin modified with mannosa 6-phosphate: a potential carrier for selective delivery of antifibrotic drugs to rat and human hepatic stellate cells,"*Hepatology*, (1999):29(5):1486-1493.
Benedetti, A. et al., "Inhibition of the Na+/H+ exchanger reduces rat hepatic stellate cell activity and liver fibrosis: an in vitro and in vivo study,"*Gastroenterology* (2001)120(2):545-56.
Blomhoff, R. et al., "Newly administered [³H] retinol is transferred from hepatocytes to stellate cells in liver for storage,"*Experimental Cell Research* (1984) 150:186-193.
Blomhoff, R. et al., "Hepatic uptake of [³H] retinol bound to the serum retinol binding protein involves both parenchymal and perisinusoidal stellate cells,"*The Journal of Biological Chemistry* (1985) 260(25): 13571-13575.
Chirila et al., "The use of synthetic polymers for delivery of therapeutic antisense oligodeoxpucleotides,"*Biomaterials* (2002) 23: 321-342.
Choi, et al., "Inhibition of tumor growth by biodegradable microspheres containing all-trans-retinoic acid in a human head-and-neck cancer xenograft,"*Int. J. Cancer* (2003) 107: 145-148.
Clark, et al. "Cationic lipid-mediated gene transfer: Current concepts,"*Curr. Opin. Mol. Ther.* (Apr. 1999) 1(2): 158-176 (abstract only).
Crooke, S.T., "Progress in antisense technology,"*Annual Review of Medicine* (2004) 55: 61-95.
Devi, G. R., "siRNA-based approaches in cancer therapy,"*Cancer Gene Therapy* (2006) 13: 819-829.
Dillard, et al., "Retinol decreases β-catenin protein levels in retinoic acid-resistant colon cancer cell lines,"*Molecular Carcinogenesis* (2007) 46:315-329.
Dixon, et al., "Nonmenclature of retinoids."*Pure & Appl. Chem.*, (1983) 55(4): 721-726.
Fingl, et al., The pharmacological basis of therapeutics, Fifth Edition, MacMillan Publishing Co, (1975) Cover and contents pages only.
Fortuna, V.A. et al., "Hepatic stellate cells uptake of retinol associated with retinol-binding protein or with bovine serum albumin,"*Journal of Cellular Biochemistry* (2003) 90(4):792-805.
Goldberg, et al., "Phase I trial of interferon a2b and liposome-Encapsulated All-trans retinoic acid in the treatment of patients with advanced renal cell carcinoma,"*Cancer* (Sep. 2002) 95(5): 1220-1227.
Greene et al, "Protective groups in organic synthesis," John Wiley & Sons, 3rd Edition (1999).
Hazen, G.G., "The synthesis of nitrogen mustard derivatives of some steroids and related compounds," Dissertation submitted for the degree of Doctor of Philosophy in the University of Michigan, Abstracts (1951) 12(4): 449.
Houglum, et al., "Two different cis-acting regulatory regions direct cell-specific transcription of the collagen a1 (1) gene in hepatic stellate cells and in skin and tendon fibroblasts,"*J. Clin. Invest.* (1995) 96: 2269-2276.
International Preliminary Report on Patentability dated Apr. 12, 2011 for International Application No. PCT/JP2009/004369, filed Sep. 4, 2009.
Jezequel, A.M. et al., "A morphological study of the early stages of hepatic fibrosis induced by low doses of dimentylnitrosame in the rat,"*J. Hepatol.* (Oct. 1987) 5(2): 174-81.
Kamps, J.A.A.M. et al., "Massive targeting ofliposomes, surface-modified with anionized albumins, to hepatic endothelial cells,"*Proceedings of the National Academy of Sciences USA* (1997) 94(21):11681-11685.

(56) References Cited

OTHER PUBLICATIONS

Kang et al., "Mannose-6 phosphateyinsulin-like growth factor-II receptor is a receptor for retinoic acid,"*Proc. Natl. Acad. Sci.* (1998) 95: 13671-13676.

Kikuchi, H., "Liposomes based on nanotechnology. Past, present and future. Part II,"*Pharm Tech Japan* (2003) 19(3):419-433.

Kim, et al., "Efficient siRNA delivery using water soluble lipopolymer for anti-angiogenic gene therapy,"*J. Controlled Release* (2007) 357-363.

Landen, et al., *Cancer Res.* (Aug. 2005) 65(15):6911.

Massaro, et al., "Noninvasive delivery of small inhibitory RNA and other reagents to pulmonary alveoli in mice,"*Am J Physiol Long Cell Mol Physiol* (2004) 287: 1066-1070.

Miao, et al., "Heat shock protein 47 and pulmonary fibrosis", *International J. Respiration* (2007) 27(22):1745-1747.

Moss, "Biochemical Nomenclature and Related Documents," Portland Press, 2nd Edition (1992) 247-251.

Nastruzzi, et al., "Liposome-associated retinoic acid increased in vitro antiproliferative effects on neoplastic cells"*FEBS Letters* (1990) 259(2):293-296.

Office Action dated Mar. 28, 2012 for U.S. Appl. No. 13/062,214, filed May 17, 2011.

Office Action dated Jul. 11, 2012 for U.S. Appl. No. 13/062,214, filed May 17, 2011.

Opalinska et al., "Nucleic-acid therapeutics: Basic principles and recent applications,"*Nature Rev.* (2002) 1: 503-514.

Pappo, et al., "Monoclonal antibody-directed targeting of fluorescent polystyrene microspheres to Peyer's patch M cells."*Immunology* (1991) 73:277-280.

Park, et al., "Retinol inhibits the growth of all-trans-retinoic acid-sensitive and *all-trans*-retinoic acid-resistant colon cancer cells through a retinoic acid receptor-independent mechanism,"*Cancer Res.* (Nov. 2005) 65:9923-9933.

Peracchi, et al., "Prospects for antiviral ribozymes and deoxyribozymes,"*Rev. Med. Virolo.* (2004) 14: 47-64.

"Remington's Pharmaceutical Sciences," 18th Edition, Mack Publishing Company (1990).

Senoo, et al., "Hepatic stellate cells and alveolar septal cells,"*Respiration* (1997) 16(4): 604-615.

Senoo, "Studies of the vitamin A-storing (stellate) cell system-from molecules to the arctic area,"*Vitamins*, Japan (2006) 80(3): 105-113.

Singh et al., "Liposome encapsulated vitamin A compounds exhibit greater stability and diminished toxicity,"*Biophysical Chemistry* (1998) 73: 155-162.

Sioud, M. et al., "Cationic Liposome-mediated delivery of siRNAs in adult mice,"*Biochem Biophys Res Commun* (Dec. 26, 2003) 312(4):1221.

Socaciu, et al., "Different ways to insert carotenoids into liposomes affect structure and dynamics of the bilayer differently,"*Biophysical Chemistry* (2002) 99: 1-15.

Sun, et al., "Retinoids and their receptors in cancer development and chemoprevention,"*Crit. Rev. Onco/Hemato.* (2002) 41: 41-55.

Tabata, et al., "All-trans-retinoic acid prevents radiation- or bleomycin-induced pulmonary fibrosis", *Am J Respir Crit Care Med.* (Dec. 15, 2006) 174(12):1352-60.

Tagami et al., "The gene-slicing effect of siRNA in cationic lipoplexes is enhanced by incorporating pDNA in the complex,"*Intl. J Pharmaceutics* (Oct. 2006) 333: 62-69.

Takahashi, et al., "Effects on M5076-heptatic metastasis of retinoic acid and n-(4-hydroxphenyl)retinamide, fenretinide entrapped in sg-liposomes", *Bio. Pharm. Bull.* (2003) 26(7):1060-1063.

Torchilin, V. P. "Targeted pharmaceutical nanocarriers for cancer therapy and imaging,"*The AAPS Journal* (2007) 9(2):128-47.

UEDA et al., "Fibroblasts and their related cells,"*Respiration* (1995) 14(7): 708-712.

Wassall, et al., "Retinoid-phospholipid Interactions as studied by magnetic resonance,"*Bulletin of Magnetic Resonance* (1987) 9(3): 85-89.

Wu, J. et al., "Modification ofliposomes for liver targeting,"*Journal of Hepatology* (1996)24(6):757-763.

Zhang et al., "Cationic lipids and polymers mediated vectors for delivery of siRNA,"*J. Control Release* (2007) 123: 1-10.

Zimmermann, T.S. et al., *Nature* (May 2006) 441(7089):111-14.

* cited by examiner

* $P<0.05$

SEQUENCE LISTING

```
<160> NUMBER OF SEQ ID NOS: 13

<210> SEQ ID NO 1
<211> LENGTH: 27
<212> TYPE: RNA
<213> ORGANISM: Artificial Sequence
<220> FEATURE:
<223> OTHER INFORMATION: siRNA-A sense strand

<400> SEQUENCE: 1
uggaugggaa agaugcagaa gaaggag                                         27

<210> SEQ ID NO 2
<211> LENGTH: 27
<212> TYPE: RNA
<213> ORGANISM: Artificial Sequence
```

```
<220> FEATURE:
<223> OTHER INFORMATION: siRNA-A antisense strand

<400> SEQUENCE: 2 ccucuucug caucuuccc auccaau                                              27

<210> SEQ ID NO 3
<211> LENGTH: 27
<212> TYPE: RNA
<213> ORGANISM: Artificial Sequence
<220> FEATURE:
<223> OTHER INFORMATION: siRNA-B sense strand

<400> SEQUENCE: 3
ugucugagug gguauuuua gacagag                                             27

<210> SEQ ID NO 4
<211> LENGTH: 27
<212> TYPE: RNA
<213> ORGANISM: Artificial Sequence
<220> FEATURE:
<223> OTHER INFORMATION: siRNA-B antisense strand

<400> SEQUENCE: 4
cugucuaaaa auacccacuc agacaau                                            27

<210> SEQ ID NO 5
<211> LENGTH: 27
<212> TYPE: RNA
<213> ORGANISM: Artificial Sequence
<220> FEATURE:
<223> OTHER INFORMATION: siRNA-C sense strand

<400> SEQUENCE: 5
gaugcgagau gaguuguaga guccaag                                            27

<210> SEQ ID NO 6
<211> LENGTH: 27
<212> TYPE: RNA
<213> ORGANISM: Artificial Sequence
<220> FEATURE:
<223> OTHER INFORMATION: siRNA-C antisense strand

<400> SEQUENCE: 6
uggacucuac aacucaucuc gcaucau                                            27

<210> SEQ ID NO 7
<211> LENGTH: 27
<212> TYPE: RNA
<213> ORGANISM: Artificial Sequence
<220> FEATURE:
<223> OTHER INFORMATION: siRNA-D sense strand

<400> SEQUENCE: 7
cagaacugcc cauccuuaaa augauag                                            27

<210> SEQ ID NO 8
<211> LENGTH: 27
<212> TYPE: RNA
<213> ORGANISM: Artificial Sequence
<220> FEATURE:
<223> OTHER INFORMATION: siRNA-D antisense strand

<400> SEQUENCE: 8
aucauuuuaa ggaugggcag uucugau                                            27
```

```
<210> SEQ ID NO 9
<211> LENGTH: 27
<212> TYPE: RNA
<213> ORGANISM: Artificial Sequence
<220> FEATURE:
<223> OTHER INFORMATION: siRNA-E sense strand

<400> SEQUENCE: 9
gagacaagau gcgagaugag uuguaag                                         27

<210> SEQ ID NO 10
<211> LENGTH: 27
<212> TYPE: RNA
<213> ORGANISM: Artificial Sequence
<220> FEATURE:
<223> OTHER INFORMATION: siRNA-E antisense strand

<400> SEQUENCE: 10
uacaacucau cucgcaucuu gucucau                                         27

<210> SEQ ID NO 11
<211> LENGTH: 27
<212> TYPE: RNA
<213> ORGANISM: Artificial Sequence
<220> FEATURE:
<223> OTHER INFORMATION: Scramble siRNA sense strand

<400> SEQUENCE: 11
cgauucgcua gaccggcuuc auugcag                                         27

<210> SEQ ID NO 12
<211> LENGTH: 27
<212> TYPE: RNA
<213> ORGANISM: Artificial Sequence
<220> FEATURE:
<223> OTHER INFORMATION: Scramble siRNA antisense strand

<400> SEQUENCE: 12
gcaaugaagc cggucuagcg aaucgau                                         27

<210> SEQ ID NO 13
<211> LENGTH: 2273
<212> TYPE: DNA
<213> ORGANISM: Mus musculus

<400> SEQUENCE: 13
gagcgattgc cctgtcggtc ccggagcagc ccagcccggc ccaggtgagg ggcgggacgg     60
ccgggcgatt tggggttgcg cattggccaa gggggaacgg atcgtccaaa gcttggggtc    120
ctgacacagg tgggcagtga agatcggac ttggaactgt cacttgcctg ggttccctgg    180
agctgcggtc tagtacgcgg actgcctggt aaaccctcac aggtcctctg tggtgcacac    240
agcccacctc ccagccatgc gctctctcct tctgggcacc ttatgcctct tggccgtggc    300
cctggcagcc gaggtgaaga aacccctaga ggcggcagcc cctggtactg cggagaagct    360
aagttccaag gcgaccacac tggcagagcg cagcacaggc ctggccttca gcctatatca    420
ggcgatggcc aaagaccagg cggtggagaa catcctcctg tcacccttgg tggtggcctc    480
atccctgggt cttgtgtcac tgggtggtaa agccaccaca gcgtcgcagg cgaaggcagt    540
gctgagcgct gagaagctgc gcgatgagga ggtgcacacg gggctgggtg agctgctccg    600
ctccctcagc aactccactg cgcgcaacgt gacctgaaa ctgggcagcc gcctgtacgg    660
gcccagctcc gtgagcttcg ccgatgactt cgtgcgcagc agcaagcaac actacaactg    720
```

```
cgaacactcc aagatcaact tccgagacaa gcgcagcgcc ctgcagtcca tcaacgagtg    780
ggcctcgcag accacggacg gcaagctgcc tgaggtcacc aaggatgtgg agcgcacgga    840
tggggcactg cttgtgaacg ccatgttctt taagccacac tgggatgaga ggtttcacca    900
caggatggtg gacaaccgtg gcttcatggt gacccgctcc tatactgtgg gtgttacgat    960
gatgcaccgg acaggcctgt acaactacta tgacgacgag aaggagaagc tgcagatggt   1020
ggagatgccc ctggctcaca agctctccag cctcatcatc ctcatgcccc accatgtgga   1080
gccgctcgag cgcttggaga agctgctgac caaggagcag ctgaaggcct ggatgggaaa   1140
gatgcagaag aaggctgtcg ccatctccct gcccaagggc gtggtggagg tgacccatga   1200
cctgcagaaa catctggcag gactgggcct gaccgaagcc atcgacaaga acaaggcaga   1260
cctatcgcgc atgtctggca agaaggacct gtacctggcc agtgtgttcc acgccactgc   1320
cttcgagtgg gacaccgagg gcaaccccct tgaccaagac atctacgggc gcgaggagct   1380
gcgcagcccc aagctgttct atgccgacca ccccttcatc ttcctggtgc gagataatca   1440
gagcggctcc ttgctcttca ttggccgcct ggtccggccc aagggagaca agatgcgaga   1500
tgagttgtag agtccaagag tgggcgtggc acggcaggaa gtagccaaag gttcctgaga   1560
cacatgggtg ctattgtggg gggaggggga ggcaccaacc ctggatattc cacgggtggg   1620
gggggttgg cagtgcaaac cggaattccc atatgtctga gtgggtattt ttagacagaa    1680
tccactccta agttaggaca tggagcccag atactatgat accaaattca ggggtgtcac   1740
agccattttg ttctgccctg caagttttag atccaatctg cctcaacagt caatcagtgt   1800
tcatatttat ggccaggcat tttatctgtt agacaatcga gttgggggta gggcagccta   1860
gctcttttg tcaccatgcc ccgagccctc ctcagtcttc ctgttcaccc ctcccccagc    1920
tccctttaac cgcaaaacta ggtgctgtgg ccccagaact gcccatcctt aaaatgatcc   1980
ttgcccagcg gtgggagctg gagacagcgc atggagggg ctccctggca tacctgccct    2040
agaactgtta tgttgggcat cacagtcatg aactttttgtt tttctccctt ttttagtttt   2100
ttcaaagatg gggggagggg aaatatgagc ctttgttgct ttcaaaacga gaacagtttg   2160
tacaagtttt tttttgaata aaacttttcc aatgaaatgt tacaggtgtg tgaaagcaga   2220
ttaaagaaag aggttcccat atcattcttt ctaaaaaaaa aaaaaaaaa aaa            2273
```

AGENT FOR TREATING MYELOFIBROSIS

CROSS-REFERENCE TO RELATED APPLICATIONS

This application is a continuation-in-part of U.S. Ser. No. 13/648,578, filed Oct. 10, 2012, which is a continuation of U.S. Ser. No. 13/062,214, filed May 17, 2011, which is a national stage filing under 35 U.S.C. §371 of international application PCT/JP2009/004369, filed Sep. 4, 2009, which claims priority to Japanese Patent Application No. 2008-228338, filed Sep. 5, 2008. This application is also a continuation-in-part of U.S. Ser. No. 13/439,330, filed Apr. 4, 2012, which is a continuation of U.S. Ser. No. 11/793,736, filed Apr. 8, 2008, which is a national stage filing under 35 U.S.C. §371 of international application PCT/JP2005/023619, filed Dec. 22, 2005. The disclosures of all of the foregoing applications are hereby incorporated by reference.

REFERENCE TO SEQUENCE LISTING

The present application is being filed along with a Sequence Listing in electronic format. The Sequence Listing is provided as a file entitled KUZU1004P1.TXT, created Jun. 18, 2013, which is 9 KB in size. The information in the electronic format of the Sequence Listing is incorporated herein by reference in its entirety.

TECHNICAL FIELD

The present invention relates to a substance delivery carrier targeted to extracellular matrix-producing cells in bone marrow, as well as to an agent for treating myelofibrosis and a method for treating myelofibrosis utilizing a drug that controls the activity and growth of an extracellular matrix-producing cell in bone marrow.

BACKGROUND

Myelofibrosis is a general term referring to diseases which causes an extensive diffuse fibrosis in bone marrow, and includes primary myelofibrosis whose etiology is unknown and secondary myelofibrosis with an underlying disease.

Primary myelofibrosis belongs to a chronic myeloproliferative disorder, being characterized by the involvement of a fibrosis in bone marrow throughout the body and extramedullary hematopoiesis in liver and spleen, as well as the manifestation of leukoerythroblastosis in which immature granulocytes and erythroblasts appear in peripheral blood. The essential of the primary myelofibrosis is considered to be a monoclonal proliferation of hematopoietic cells due to genetic abnormality including Jak2 gene mutation caused at the level of hematopoietic stem cells. Various cytokines produced by the proliferated hematopoietic cells (mainly megakaryocyte) act on bone marrow stromal cells to cause a proliferation of reactive polyclonal bone marrow stromal cells, which leads the fibrosis of bone marrow, osteosclerosis and angiogenesis. This results in characteristic clinical symptoms such as an ineffective hematopoiesis, an appearance of dacryocytes in peripheral blood, leukoerythroblastosis, and an extramedullary hematopoiesis causing a splenomegaly.

Approximately 40% of the primary myelofibrosis have gene mutation in Jak2, a tyrosine kinase essential for signal transduction of cytokines, resulting in a constitutive activation of Jak2 even in the absence of a cytokine stimulation. Apart from Jak2, there are a few cases with genetic mutation in c-mpl (a thrombopoietin receptor).

It is currently considered to be difficult to cure primary myelofibrosis by drug therapy, and an allogeneic transplantation of hematopoietic stem cells is the sole curative therapy. However, the mortality rate associated with transplant is as high as 25 to 48%, limiting the total survival rate to around 50%. Recently, the utility of nondisruptive transplant of bone marrow stem cells (mini-transplant) with less treatment-associated toxicity has been highlighted, yet only a limited number of cases has been studied and their long-term prognoses are yet to be known.

As drug therapy, although being palliative, the effectiveness of anabolic hormones such as danazol and Primobolan, angiogenesis inhibitor such as thalidomide and lenalidomide, anti-tumor drug such as hydroxycarbamide, anagrelide, imatinib, 2-chlorodeoxyadenosine, melphalan, busulfan and etoposide, and other drugs such as erythropoietin, for anemia, thrombocytopenia and splenomegaly has been shown (see Non-Patent Literatures 1 and 2).

On the other hand, secondary myelofibrosis is those which occur secondary to a disease such as acute myeloid leukemia, acute lymphocytic leukemia, chronic myeloid leukemia, polycythemia vera, primary thrombocythemia, myelodysplastic syndrome, multiple myeloma, malignant lymphoma, carcinoma, systemic lupus erythematosus and progressive systemic sclerosis, or radiation, and shows a similar bone marrow image to primary myelofibrosis. Treatment for the secondary myelofibrosis is focused on improving the underlying disease. However, many of these underlying diseases are difficult to be radically cured. Thus, there is a strong need for alleviating the adverse effect due to myelofibrosis itself.

In those circumstances, a great deal of investigation has been made for the development of myelofibrosis therapeutics. As a result, there have been reports that successes to a certain extent were provided in animal models of myelofibrosis or in clinical trials by, for example, inhibitors of a tyrosine kinase JAK2V617F, TGF-β inhibitors such as soluble TGF-β receptor, NFκB inhibitors such as bortezomib, DNA methyltransferase inhibitors such as decitabine, histone deacetylase inhibitors such as trichostatin A, VEGF inhibitors such as PTK787/ZK222584 and bevacizumab (see Non-Patent Literature 1) and certain types of anti-human lymphocyte antibody (see Patent Literature 1). However, none of these drugs are satisfactory, and development of further agent for treating myelofibrosis has been longed.

Patent Literature 1: JP A No. 8-002799
Patent Literature 2: WO 2006/068232
Non-Patent Literature 1: Hematology Am Soc Hematol Educ Program. 2007; 2007:346-54.
Non-Patent Literature 2: The Journal of the Japanese Society of Internal Medicine, Vol. 96, No. 7, Jul. 10, 2007, pp. 1398-1404.

Problems to be Solved by the Invention

The present invention is aimed to provide a novel agent for treating myelofibrosis and a method for treating myelofibrosis.

Means for Solving the Problems

The inventors have discovered, through the exploration for a novel therapeutic agent for myelofibrosis, that myelofibrosis could effectively be treated by administering a composition in which an extracellular matrix production inhibitor is carried by a carrier comprising a retinoid, thereby completed the invention.

While it has been known that a carrier comprising vitamin A can deliver a drug to stellate cells that store vitamin A (see Patent Literature 2), its relation to myelofibrosis has been completely unknown to date. Nor has there been any report that myelofibrosis could be treated by a composition comprising as an active ingredient an extracellular matrix production inhibitor. Therefore, the current findings are quite surprising.

Namely, the present invention relates to the following:
(1) A substance delivery carrier for the delivery of a substance to an extracellular matrix-producing cell in bone marrow, comprising a retinoid as a targeting agent.
(2) The carrier according to (1), wherein the retinoid comprises retinol.
(3) The carrier according to (1) or (2), wherein the retinoid content is 0.2-20 wt % of the entire carrier.
(4) The carrier according to any one of (1) to (3), wherein the carrier has a form of a liposome, and the molar ratio of the retinoid to the lipid contained in the liposome is 8:1-1:4.
(5) A composition for treating myelofibrosis, comprising a drug that controls the activity or growth of an extracellular matrix-producing cell in bone marrow.
(6) The composition according to (5), further comprising the carrier according to any one of (1) to (4).
(7) The composition according to (5) or (6), wherein the drug that controls the activity or growth of an extracellular matrix-producing cell in bone marrow is selected from the group consisting of an agent for inhibiting activity or production of a bioactive substance selected from the group consisting of gelatinase A, gelatinase B and angiotensinogen, an inhibitor of cell activity, a growth inhibitor, an apoptosis-inducing agent, as well as an siRNA, a ribozyme, an antisense nucleic acid, and a DNA/RNA chimeric polynucleotide which target at least one of extracellular matrix constituent molecules or molecules involved in the production or secretion of said extracellular matrix constituent molecules, and a vector that expresses said siRNA, ribozyme, antisense nucleic acid, and DNA/RNA chimeric polynucleotide.
(8) The composition according to (7), wherein the molecule involved in the production or secretion of the extracellular matrix constituent molecules is HSP47.
(9) The composition according to any one of (5) to (8), wherein the drug and the carrier are mixed at a place of medical treatment or in its vicinity.
(10) A kit for preparing a composition according to any one of (6) to (9), comprising one or more containers that comprise either singly or in combination the drug that controls the activity or growth of an extracellular matrix-producing cell in bone marrow, the retinoid, and if necessary, a carrier-constituent substance other than the retinoid.
(11) An siRNA targeted to a part of a nucleotide sequence of SEQ ID NO: 13, wherein the part being selected from position 1130 to position 1145, position 1485 to position 1500, position 1501 to position 1516, position 1654 to position 1678 and position 1951 to position 1978 of the nucleotide sequence of SEQ ID NO: 13.
(12) The siRNA according to (11), consisting of any one of the following combinations A to E of a sense strand and an antisense strand:

A: a combination of
    (sense strand, SEQ ID NO: 1)
5'-UGGAUGGGAAAGAUGCAGAAGAAGGAG-3'
and
    (antisense strand, SEQ ID NO: 2)
3'-UAACCUACCCUUUCUACGUCUUCUUCC-5', B: a combination of
    (sense strand, SEQ ID NO: 3)
5'-UGUCUGAGUGGGUAUUUUUAGACAGAG-3'
and
    (antisense strand, SEQ ID NO: 4)
3'-UAACAGACUCACCCAUAAAAAUCUGUC-5', C: a combination of
    (sense strand, SEQ ID NO: 5)
5'-GAUGCGAGAUGAGUUGUAGAGUCCAAG-3'
and
    (antisense strand, SEQ ID NO: 6)
3'-UACUACGCUCUACUCAACAUCUCAGGU-5', D: a combination of
    (sense strand, SEQ ID NO: 7)
5'-CAGAACUGCCCAUCCUUAAAAUGAUAG-3'
and
    (antisense strand, SEQ ID NO: 8)
3'-UAGUCUUGACGGGUAGGAAUUUUACUA-5', E: a combination of
    (sense strand, SEQ ID NO: 9)
5'-GAGACAAGAUGCGAGAUGAGUUGUAAG-3'
and
    (antisense strand, SEQ ID NO: 10)
3'-UACUCUGUUCUACGCUCUACUCAACAU-5'.

SUMMARY

The Effects of the Invention

While the exact mechanism of action of the composition for treating myelofibrosis of the present invention has not yet been completely clarified, the mechanism is considered as follows: with the composition, retinoid functions as a targeting agent to extracellular matrix-producing cells in bone marrow such as bone marrow fibroblasts, and delivers active ingredients such as pharmaceutical agents that control activity or growth of extracellular matrix-producing cells in bone marrow to such cells, thereby exhibiting the effect against myelofibrosis.

Since active ingredients can be efficiently delivered to a site of action and further to a target cell, by using the carrier of the present invention, the treatment, suppression of progression, and prevention of onset of myelofibrosis, in particular primary myelofibrosis, the treatment of which has been difficult to date, are enabled; thus, the present carrier significantly contributes to the human medicine and veterinary medicine.

Furthermore, since the composition of the present invention comprises as an active agent a drug that controls the activity or growth of an extracellular matrix-producing cell whose effectiveness to myelofibrosis has not been known, it can treat myelofibrosis by a different mechanism from those currently known. Therefore, it is expected to ameliorate pathologic conditions which could not be treated by drugs of conventional mechanism, and to increase the therapeutic effect of the combined use with those conventional drugs.

Moreover, the carrier of the present invention can be combined with any pharmaceutical drugs (for example, existing therapeutic agents for myelofibrosis) to increase their action efficiency; therefore, it is also advantageous for its broad range of application in terms of formulation, facilitating the production of effective therapeutic agents.

DETAILED DESCRIPTION OF EMBODIMENTS

Figure 1:
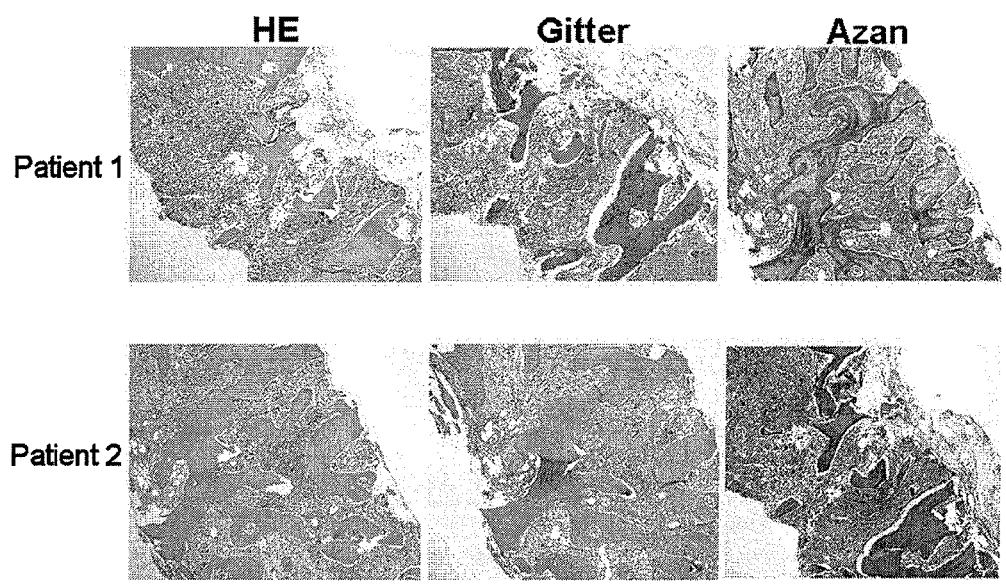
FIG. 1 shows photographs showing bone marrow images of ideopathic myelofibrosis patients. Both Patient 1 and Patient 2 showed trabecular thickening by HE staining (left column), reticular fiber hyperplasia by Gitter staining (central column) and collagen deposition by Azan staining (right column).

The present invention relates to a substance delivery carrier for the delivery of the substance to an extracellular matrix-producing cell in bone marrow, comprising a retinoid as a targeting agent.

In the present invention, the extracellular matrix-producing cell in bone marrow is not particularly limited as long as it is a cell being present in bone marrow and having a capability of producing extracellular matrix, and it typically includes a bone marrow fibroblast. A bone marrow fibroblast is characterized by the expression of α-SMA (alpha-smooth muscle actin). The bone marrow fibroblast in the present invention is one of those identified, e.g., by immunostaining using detectably-labeled anti-α-SMA antibodies.

The retinoid of the present invention is not particularly limited as long as it promotes delivery of a substance to an extracellular matrix-producing cell in bone marrow, and examples thereof include retinoid derivatives such as retinol (vitamin A), etretinate, tretinoin, isotretinoin, adapalene, acitretine, tazarotene, and retinol palmitate, as well as vitamin A analogues such as fenretinide (4-HPR, 4-hydroxyphenylretinamide) and bexarotene.

The retinoid of the present invention is one of those which promote a specific delivery of a substance to an extracellular matrix-producing cell in bone marrow. The mechanism of the promotion of substance delivery by retinoid has not yet been completely clarified; however, for example, it is considered that a retinoid which has specifically bound to a retinol-binding protein (RBP) is taken into an extracellular matrix-producing cell in bone marrow through a certain receptor present on the surface of this cell.

A retinoid is a member of a class of compounds having a skeleton in which four isoprenoid units are bonded in a head-to-tail manner (see G. P. Moss, "Biochemical Nomenclature and Related Documents," 2nd Ed. Portland Press, pp. 247-251 (1992)). Vitamin A is a generic descriptor for a retinoid that qualitatively shows the biological activity of retinol. Retinoid that can be used in the present invention is not particularly limited, and examples thereof include retinoid derivatives such as retinol, retinal, retinoic acid, an ester of retinol and a fatty acid, an ester of an aliphatic alcohol and retinoic acid, etretinate, tretinoin, isotretinoin, adapalene, acitretine, tazarotene and retinol palmitate, and vitamin A analogues such as fenretinide (4-HPR) and bexarotene.

Of these, retinol, retinal, retinoic acid, an ester of retinol and a fatty acid (such as retinyl acetate, retinyl palmitate, retinyl stearate and retinyl laurate) and an ester of an aliphatic alcohol and retinoic acid (such as ethyl retinoate) are preferable from the viewpoint of efficiency of specific delivery of a substance to extracellular matrix-producing cells in bone marrow.

All retinoid isomers including cis-trans isomers are included in the scope of the present invention. The retinoid may be substituted with one or more substituents. The retinoid in the present invention includes a retinoid in an isolated form as well as in a form of a solution or mixture with a medium that can dissolve or retain the retinoid.

The carrier of the present invention may be constituted from the retinoid on its own or may be constituted by binding the retinoid to a carrier-constituent component other than the retinoid, or by enclosing the retinoid in a carrier-constituent component other than the retinoid. Therefore, the carrier of the present invention may comprise a carrier-constituent component other than the retinoid. Such a component is not particularly limited, and any component known in the medicinal and pharmaceutical fields may be used, but those that can enclose the retinoid or can bind to the retinoid are preferable.

Examples of such a component include a lipid, for example, a phospholipid such as glycerophospholipid, a sphingolipid such as sphingomyelin, a sterol such as cholesterol, a vegetable oil such as soybean oil or poppy seed oil, a mineral oil, and a lecithin such as egg-yolk lecithin, but the examples are not limited thereto. Among them, those that can form a liposome are preferable, for example, a natural phospholipid such as lecithin, a semisynthetic phospholipid such as dimyristoylphosphatidylcholine (DMPC), dipalmitoylphosphatidylcholine (DPPC), or distearoylphosphatidylcholine (DSPC), and dioleylphosphatidylethanolamine (DOPE), dilauroylphosphatidylcholine (DLPC), and cholesterol.

A particularly preferred component is a component that can avoid capture by the reticuloendothelial system, and examples thereof include cationic lipids such as N-α-trimethylammonioacetyl)-didodecyl-D-glutamate chloride (TMAG), N,N',N'',N'''-tetramethyl-N,N',N'',N'''-tetrapalmitylspermine (TMTPS), 2,3-dioleyloxy-N-[2(sperminecarboxamido)ethyl]-N,N-dimethyl-1-propanaminium trifluoroacetate (DOSPA), N-[1-(2,3-dioleyloxy)propyl]-N,N,N-trimethylammonium chloride (DOTMA), dioctadecyldimethylammonium chloride (DODAC), didodecylammonium bromide (DDAB), 1,2-dioleyloxy-3-trimethylammoniopropane (DOTAP), 3β-[N—(N',N'-dimethylaminoethane)carbamoyl]cholesterol (DC-Chol), 1,2-dimyristoyloxypropyl-3-dimethylhydroxyethylammonium bromide (DMRIE), and O,O'-ditetradecanoyl-N-α-trimethylammonioacetyl)diethanolamine chloride (DC-6-14).

The binding of the retinoid to the carrier of the present invention or the enclosing of it therein is also made possible by binding the retinoid to or enclosing it in a carrier constituent other than the retinoid by a chemical and/or physical method. Alternatively, the retinoid can be bound to or enclosed in the carrier of the present invention by mixing the retinoid and the carrier constituents other than the retinoid during the preparation of the carrier. The amount of the retinoid bound to or enclosed in the carrier of the present invention may be, as a weight ratio in the carrier-constituent components, 0.01% to 100%, preferably 0.2% to 20%, and more preferably 1% to 5%. The retinoid may be bound to or enclosed in the carrier before loading a drug to the carrier; or the carrier, retinoid and drug may simultaneously be mixed; or the retinoid may be admixed with the carrier already carrying the drug, etc. Therefore, the present invention also relates to a process for producing a formulation specific to an extracellular matrix-producing cell in bone marrow, the process comprising a step of binding a retinoid to any existing drug-binding carrier or drug-encapsulating carrier, for example, a liposomal formulation such as DaunoXome®, Doxil, Caelyx®, or Myocet®.

The carrier of the present invention may be in any form as long as a desired substance or object can be transported to a target extracellular matrix-producing cell in bone marrow, and although not limited thereto, examples thereof include a macromolecular micelle, a liposome, an emulsion, microspheres, and nanospheres. In the present invention, a liposomal form is preferable among these from the viewpoint of a high delivery efficiency, a wide selection of substances to be delivered, and an ease of formulation, etc., and a cationic liposome including a cationic lipid is particularly preferable. In the case where the carrier is in a form of a liposome, the molar ratio of the retinoid to other constituents of the liposome is preferably 8:1 to 1:4, more preferably 4:1 to 1:2, yet more preferably 3:1 to 1:1, and particularly preferably 2:1, considering the efficiency in retinoid's binding to or enclosure in the carrier.

The carrier of the present invention may contain a substance to be transported within its interior, may be attached to the exterior of a substance to be transported, or may be mixed with a substance to be transported, as long as it comprises retinoid in a form such that the retinoid is able to function as a targeting agent. "Function as a targeting agent" herein means that the carrier comprising a retinoid reaches and/or is taken up by the target cell, i.e., an extracellular matrix-producing cell in bone marrow, more rapidly and/or in a larger quantity than with a carrier not comprising the retinoid, and this may easily be confirmed by, for example, adding a labeled carrier or label-containing carrier to a culture of target cells and analyzing the distribution of the label after a predetermined period of time. Structurally, this requirement can be satisfied, for example, if retinoid is at least partially exposed to the exterior of the formulation containing the carrier at the latest by the time it reaches the target cell. Whether or not the retinoid is exposed at the exterior of a formulation can be evaluated by contacting the formulation to a substance that specifically binds to retinoid, such as a retinol-binding protein (RBP), and evaluating its binding to the formulation.

The substance or object that is delivered by the present carrier is not particularly limited, and it preferably has a size such that it can physically move within the body of an organism from the site of administration to the site of lesion where the target cell is present. Therefore, the carrier of the present invention can transport not only a substance such as an atom, a molecule, a compound, a protein, or a nucleic acid, but also an object such as a vector, a virus particle, a cell, a drug-releasing system consisting of one or more elements, or a micromachine. The substance or object preferably has the property of having some influence on the target cell, for example, labeling the target cell or controlling (e.g. increasing or suppressing) the activity or growth of the target cell.

Therefore, in one embodiment of the present invention, what is delivered by the carrier is "a drug that controls the activity or growth of an extracellular matrix-producing cell in bone marrow". The activity of the extracellular matrix-producing cell in bone marrow herein refers to various activities such as secretion, uptake or migration exhibited by an extracellular matrix-producing cell in bone marrow, and in the present invention, in particular, among these, it typically means an activity involved in the onset, progression, and/or recurrence of myelofibrosis. Examples of such activities include, but are not limited to, the production/secretion of a bioactive substance such as gelatinase A and gelatinase B (MMP2 and MMP9, respectively) and angiotensinogen, and of an extracellular matrix component such as collagen, proteoglycan, tenascin, fibronectin, thrombospondin, osteopontin, osteonectin and elastin.

Therefore, the drug that controls the activity or growth of an extracellular matrix-producing cell in bone marrow may be any drug that directly or indirectly suppresses the physical, chemical and/or physiological actions of said cell related to the onset, progression and/or recurrence of myelofibrosis, and including while not being limited to: a drug that inhibits the activity or production of the bioactive substances above, a MMP inhibitor such as batimastat, and antibodies and antibody fragments that neutralize the bioactive substances above, and a substance that suppresses the expression of the bioactive substances above, such as an siRNA, a ribozyme, an antisense nucleic acid (including RNA, DNA, PNA (peptide nucleic acid), or a composite thereof), or a substance having a dominant negative effect such as a dominant negative mutant, or a vector expressing these, or a drug that inhibits the production and secretion of the extracellular matrix component above, for example, a substance that suppresses the expression of the extracellular matrix component, such as an siRNA, a ribozyme, an antisense nucleic acid (including RNA, DNA, PNA, or a composite thereof), or a substance having a dominant negative effect such as a dominant negative mutant, or a vector expressing these, an inhibitor of cell activity such as a sodium channel blocker, cell-growth inhibitors such as an alkylating agent (such as ifosfamide, nimustine, cyclophosphamide, dacarbazine, melphalan, and ranimustine), an antitumor antibiotic (such as idarubicin, epirubicin, daunorubicin, doxorubicin, pirarubicin, bleomycin, peplomycin, mitoxantrone, and mitomycin C), an antimetabolite (such as gemcitabine, enocitabine, cytarabine, tegafur/uracil, a tegafur/gimeracil/oteracil potassium mixture, doxifluridine, hydroxycarbamide, fluorouracil, methotrexate, and mercaptopurine), an alkaloid such as etoposide, irinotecan hydrochloride, vinorelbine ditartrate, docetaxel hydrate, paclitaxel, vincristine sulfate, vindesine sulfate, and vinblastine sulfate, and platinum complexes such as carboplatin, cisplatin, and nedaplatin, as well as apoptosis inducers such as compound 861, gliotoxin, lovastatin, and Beractant. Furthermore, the "drug that controls the activity or growth of an extracellular matrix-producing cell in bone marrow" in the present invention may be any drug that directly or indirectly promotes the physical, chemical and/or physiological actions of an extracellular matrix-producing cell in bone marrow directly or indirectly related to the suppression of onset, progression and/or recurrence of myelofibrosis.

Among the "drug that controls the activity or growth of an extracellular matrix-producing cell in bone marrow" in the present invention, preferences are given to the drugs that inhibit the production/secretion of the extracellular matrix component, for example, collagen, proteoglycan, tenascin, fibronectin, thrombospondin, osteopontin, osteonectin and elastin, and particularly preferably, inhibitors against Heat Shock Protein 47 (HSP47), inter alia, siRNA against HSP47.

The substance delivered by the carrier of the invention include, without limitation, drugs which suppress the onset, progression and/or recurrence of myelofibrosis and which have not been mentioned above, and examples include, without limitation, anabolic hormones such as danazol and Primobolan, angiogenesis inhibitors such as thalidomide and lenalidomide, antitumor drugs such as hydroxycarbamide, anagrelide, imatinib, 2-chlorodeoxyadenosine, melphalan, busulfan and etoposide, erythropoietin, inhibitors of JAK2V617F tyrosine kinase, TGF-β inhibitors such as soluble TGF-β receptor, NFκB inhibitors such as bortezomib, DNA methyltransferase inhibitors such as decitabine, histone deacetylase inhibitors such as trichostatin A, VEGF inhibitors such as PTK787/ZK222584 and bevacizumab, and anti-human lymphocyte antibody described in Patent literature 1 above.

The substance or object delivered by the carrier of the present invention may or may not be labeled. Labeling enables monitoring of the success or failure of transport, or increases and decreases in target cells, etc., and is particularly useful at the testing/research level. A label may be selected from any label known to a person skilled in the art such as, for example, any radioisotope, magnetic material, substance that binds to a labeled substance (e.g. an antibody), fluorescent substance, fluorophore, chemiluminescent substance, and enzyme, etc.

In the present invention, "to an extracellular matrix-producing cell in bone marrow" or "for the delivery to an extracellular matrix-producing cell in bone marrow" means that it is suitable to use to the extracellular matrix-producing cells as a target cell, and this includes, for example, that it is possible to deliver a substance to this cell, more rapidly, efficiently, and/or in a larger quantity than to other cells, for example, normal cells. For example, the carrier of the present invention can deliver a substance to an extracellular matrix-producing cell in bone marrow at a rate and/or efficiency of 1.1 times or more, 1.2 times or more, 1.3 times or more, 1.5 times or more, 2 times or more, or even 3 times or more compared with other cells.

The present invention also relates to a composition for controlling the activity or growth of an extracellular matrix-producing cell in bone marrow, or for treating myelofibrosis, the composition comprising the drug that controls the activity or growth of the extracellular matrix-producing cell in bone marrow, and the present invention also relates to a use of the drug that controls the activity or growth of the extracellular matrix-producing cell in bone marrow in the production of said compositions. The drug may be contained in the composition alone or together with a pharmaceutically acceptable carrier. The composition of the present invention may be targeted to an extracellular matrix-producing cell in bone marrow, which will be the target, for efficient delivery to said cell. The way of targeting is not particularly limited as long as it promotes the delivery of the composition of the present invention to an extracellular matrix-producing cell in bone marrow, e.g., a bone marrow fibroblast, and examples includes the addition of a retinoid. Accordingly, a preferred embodiment of the present invention includes a retinoid as a targeting agent, and more preferably, includes a carrier comprising above-mentioned retinoid as a targeting agent.

In the present invention, myelofibrosis includes primary myelofibrosis as well as secondary myelofibrosis. Secondary myelofibrosis includes, without limitation, those which occur secondary to a disease such as acute myeloid leukemia, acute lymphoid leukemia, chronic myeloid leukemia, polycythemia vera, primary thrombocythemia, myelodysplastic syndrome, multiple myeloma, malignant lymphoma, carcinoma, systemic lupus erythematosus and progressive systemic sclerosis, or to radiation.

Myelofibrosis in the present invention can be diagnosed by any methods known in the art. The most characteristic pathology of myelofibrosis is a fibrillization of bone marrow, and this can be determined to some extent by a failure in collecting of bone marrow aspirate by bone marrow aspiration ("dry tap"). A definitive diagnosis is made by confirming the fibrillization of bone marrow and/or an increase in trabecula by bone marrow biopsy (see FIG. 1). Primary myelofibrosis may further manifest anemia, hepatosplenomegaly, appearances of leukoerythroblastosis, poikilocytes such as dacryocytes, blast cells, macrothrombocytes and megakaryocytes in peripheral blood, an increase in serum LDH, an increase in hepatosplenic uptake by bone marrow scintigraphy, occasional bleeding tendency, abdominal bloating, fever, general malaise, loss of body weight, etc. In secondary myelofibrosis, the symptoms of the underlying disease often come to the fore. Specific symptoms of an underlying disease are well known by those skilled in the art.

In the composition of the present invention, as long as the retinoid contained in the carrier is present in a mode such that it functions as a targeting agent, the carrier may contain a substance to be delivered within its interior, may be attached to the exterior of a substance to be delivered, or may be mixed with a substance to be delivered. Therefore, depending on the administration route and the manner in which the drug is released, etc., the composition may be covered with an appropriate material such as, for example, an enteric coating or a timed-disintegrating material, or may be incorporated into an appropriate drug release system.

The composition of the present invention may be administered via various routes including both oral and parenteral routes, and examples thereof include, but are not limited to, oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal, and intrauterine routes, and it may be formulated into a dosage form suitable for each administration route. Such a dosage form and formulation method may be selected as appropriate from any known dosage forms and methods (see e.g. Hyojun Yakuzaigaku (Standard Pharmaceutics), Ed. by Yoshiteru Watanabe et al., Nankodo, 2003).

Examples of dosage forms suitable for oral administration include, but are not limited to, powder, granule, tablet, capsule, liquid, suspension, emulsion, gel, and syrup, and examples of the dosage form suitable for parenteral administration include injections such as an injectable solution, an injectable suspension, an injectable emulsion, and an injection to be prepared immediately before use. Formulations for parenteral administration may be in a form such as an aqueous or nonaqueous isotonic sterile solution or suspension.

The composition of the present invention may comprise one or more of any other drugs that may cure myelofibrosis or alleviate the onset, progress and/or recurrence and/or symptoms thereof, or may be used in combination of such drugs. The examples of such drugs include, without limitation, for example, anabolic hormones such as danazol and Primobolan, angiogenesis inhibitor such as thalidomide and lenalidomide, anti-tumor drug such as hydroxycarbamide, anagrelide, imatinib, 2-chlorodeoxyadenosine, melphalan, busulfan and etoposide, erythropoietin, inhibitors of JAK2V617F tyrosine kinase, TGF-β inhibitors such as soluble TGF-β receptor, NFκB inhibitors such as bortezomib, DNA methyltransferase inhibitors such as decitabine, histone deacetylase inhibitors such as trichostatin A, VEGF inhibitors such as PTK787/ZK222584 and bevacizumab, and anti-human lymphocyte antibody described in Patent literature 1 above. When used in combination, the composition of the present invention may be administered simultaneously with, before or after the other drug. The administration route can be the same or different. For example, the composition of the present invention may be administered parenterally, whereas the other drug may be administered orally, etc.

The carrier or the composition of the present invention may be provided in any form, but from the viewpoint of storage stability, it is preferably provided in a form that can be prepared immediately before use, for example in a form such that it can be prepared at a place of medical treatment or in the vicinity thereof by a doctor and/or pharmacist, nurse or other paramedic. In this case, the carrier or the composition of the present invention is provided as one or more containers containing at least one constituent essential for it, and it is prepared prior to use, for example, within 24 hours prior to use, preferably within 3 hours prior to use, and more preferably, immediately prior to use. When preparing, a reagent, a solvent, preparation equipment, etc. that are normally available in the place of preparation may be used as appropriate.

Accordingly, the present invention also relates to a kit for preparing a carrier or composition, the kit comprising one or more containers that contain singly or in combination a retinoid, and/or a substance to be delivered, and/or a carrier-constituent substance other than the retinoid, as well as to a constituent that is necessary for the carrier or composition, provided in a form of such kit. The kit of the present invention may comprise, in addition to the above, instructions, an electronic recording medium such as a CD or DVD regarding methods for preparing or administrating the carrier and composition of the present invention, etc. Furthermore, the kit of the present invention may comprise all of the constituents for completing the carrier or the composition of the present invention, but need not necessarily to comprise all of the constituents. Accordingly, the kit of the present invention need not comprise a reagent or solvent that is normally available at a place of medical treatment or experimental facility, etc., such as, for example, sterile water, physiological saline or glucose solution.

The present invention further relates to a method for controlling the activity or growth of an extracellular matrix-producing cell in bone marrow, or a method for treating myelofibrosis, the method comprising administering an effective amount of foregoing composition to a subject in need thereof. The effective amount herein, in a method for treating myelofibrosis, for example, is an amount that suppresses the onset or recurrence of myelofibrosis, alleviates its symptoms, or delays or brings to a halt its progression, and is preferably an amount that prevents the onset or recurrence of myelofibrosis or cures it. It is also preferably an amount that does not cause an adverse effect that exceeds the benefit from administration. Such an amount may appropriately be determined by an in vitro test using cultured cells or by a test in a model animal such as a mouse, rat, dog or pig, and such test methods are well known to a person skilled in the art. Moreover, the dose of the retinoid contained in the carrier and the dose of the drug used in the method of the present invention are known to a person skilled in the art, or may appropriately be determined by the above-mentioned test, etc.

The specific dose of the composition administered in the method of the present invention may be determined in view of various conditions with respect to the subject in need of the treatment, such as the severity of symptoms, general health condition of the subject, age, body weight, gender of the subject, diet, the timing and frequency of administration, a concurrent medicament, responsiveness to the treatment, and the compliance with the treatment, etc.

The route of administration includes various routes including both oral and parenteral routes, for example, such as oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal and intrauterine routes.

The frequency of administration varies depending on the properties of the composition to be used and the aforementioned conditions of the subject, and may be, for example, a plurality of times per day (i.e., 2, 3, 4, 5, or more times per day), once a day, every few days (i.e., every 2, 3, 4, 5, 6, or 7 days, etc.), a few times per week (e.g. 2, 3, 4 times, etc. per week), once a week, or every few weeks (i.e., every 2, 3, 4 weeks, etc.).

In the method of the present invention, the term "subject" means any living individual, preferably an animal, more preferably a mammal, and yet more preferably a human individual. In the present invention, the subject may be healthy or affected by some disorder, and when treatment of myelofibrosis is intended, it typically means a subject affected by myelofibrosis or at a risk of being affected by myelofibrosis. When prevention of primary myelofibrosis is intended, for example, typical examples include, without limitation, a subject having a gene mutation in Jak2 and/or c-mpl. When prevention of secondary myelofibrosis is intended, typical examples include, without limitation, a subject being affected by a disease such as acute myeloid leukemia, acute lymphoid leukemia, chronic myeloid leukemia, polycythemia vera, primary thrombocythemia, myelodysplastic syndrome, multiple myeloma, malignant lymphoma, carcinoma, systemic lupus erythematosus or progressive systemic sclerosis, or a subject who has undergone irradiation.

Furthermore, the term "treatment" includes all types of medically acceptable prophylactic and/or therapeutic intervention for the purpose of the cure, temporary remission or prevention of a disorder. For example, the term "treatment" includes medically acceptable intervention of various purposes, including delaying or halting the progression of myelofibrosis, regression or disappearance of a lesion, prevention of onset and prevention of recurrence of myelofibrosis.

The present invention also relates to a method utilizing the above carrier for delivering a drug to an extracellular matrix-producing cell in bone marrow. This method includes, but is not limited to, for example, a step of loading a substance to be delivered onto the carrier, and a step of administering or adding the carrier carrying the substance to be delivered to an organism or a medium, for example a culture medium, which contains an extracellular matrix-producing cell in bone marrow. These steps may appropriately be achieved according to any known method or such as a method described in the present specification. The delivery method may be combined with another delivery method, for example, another delivery method for targeting bone marrow. Moreover, the method includes an embodiment performed in vitro and an embodiment in which an extracellular matrix-producing cell in bone marrow inside the body is targeted.

The present invention also relate to a novel siRNA against mouse HSP47, preferably those targeted to the part selected from position 1130 to position 1145, position 1485 to position 1500, position 1501 to position 1516, position 1654 to position 1678 and position 1951 to position 1978 of SEQ. ID NO: 13. Although methods for designing and producing an siRNA against specific region of a gene for suppressing the expression of said gene are known in the art, it is generally impossible to predict the part of the gene which should be targeted, and this can only be ascertained via experiment. In the present invention, for their strong suppressive effect on HSP47 expression, an siRNA that targets to position 1501 to position 1516, and an siRNA that targets to position s 1951 to position 1978 of SEQ ID NO: 13 are preferred. Some preferred examples of the novel siRNAs of the present invention consist of following combinations of sense strand and antisense strand.

```
Sequences A: a combination of:
                            (sense, SEQ ID NO: 1)
5'-UGGAUGGGAAAGAUGCAGAAGAAGGAG-3'
and (antisense, SEQ ID NO: 2)
3'-UAACCUACCCUUUCUACGUCUUCUUCC-5'.

Sequences B: a combination of:
                            (sense, SEQ ID NO: 3)
5'-UGUCUGAGUGGGUAUUUUUAGACAGAG-3'
and (antisense, SEQ ID NO: 4)
3'-UAACAGACUCACCCAUAAAAAUCUGUC-5'.

Sequences C: a combination of:
                            (sense, SEQ ID NO: 5)
5'-GAUGCGAGAUGAGUUGUAGAGUCCAAG-3'
and (antisense, SEQ ID NO: 6)
3'-UACUACGCUCUACUCAACAUCUCAGGU-5'.

Sequences D: a combination of:
                            (sense, SEQ ID NO: 7)
5'-CAGAACUGCCCAUCCUUAAAAUGAUAG-3'
and (antisense, SEQ ID NO: 8)
3'-UAGUCUUGACGGGUAGGAAUUUUACUA-5'.

Sequences E: a combination of:
                            (sense, SEQ ID NO: 9)
5'-GAGACAAGAUGCGAGAUGAGUUGUAAG-3'
and (antisense, SEQ ID NO: 10)
3'-UACUCUGUUCUACGCUCUACUCAACAU-5'.
```

Among these, Sequences C and D are particularly preferred for their strong suppressive effect on HSP47 expression.

The siRNA of the present invention may have a naturally occurring RNA structure, or may also have various modifications aimed to improve in vivo stability or binding affinity to the target sequence. Such modification includes, without limitation, a modification by a terminal amino group, thiol group, cholesterol, long-chain alkyl, sugar chain or peptide, etc., a formation of abasic site, an introduction of modified nucleic acid such as a locked nucleic acid (LNA), a peptide nucleic acid (PNA), a nucleotide modified at 2' position of the sugar, for example, 2'-O-alkyl-, 2'-O-alkyl-O-alkyl- or 2'-fluoro-modified nucleotide.

The siRNA of the present invention is extremely useful for suppressing HSP47 expression in a mouse and for suppressing collagen production associated with HSP47 expression, and can particularly be suitable for the use in researches, experiments and tests using a mouse.

EXAMPLES

Example 1

Confirmation of Pathology in Myelofibrosis Model Mice

Figure 2:
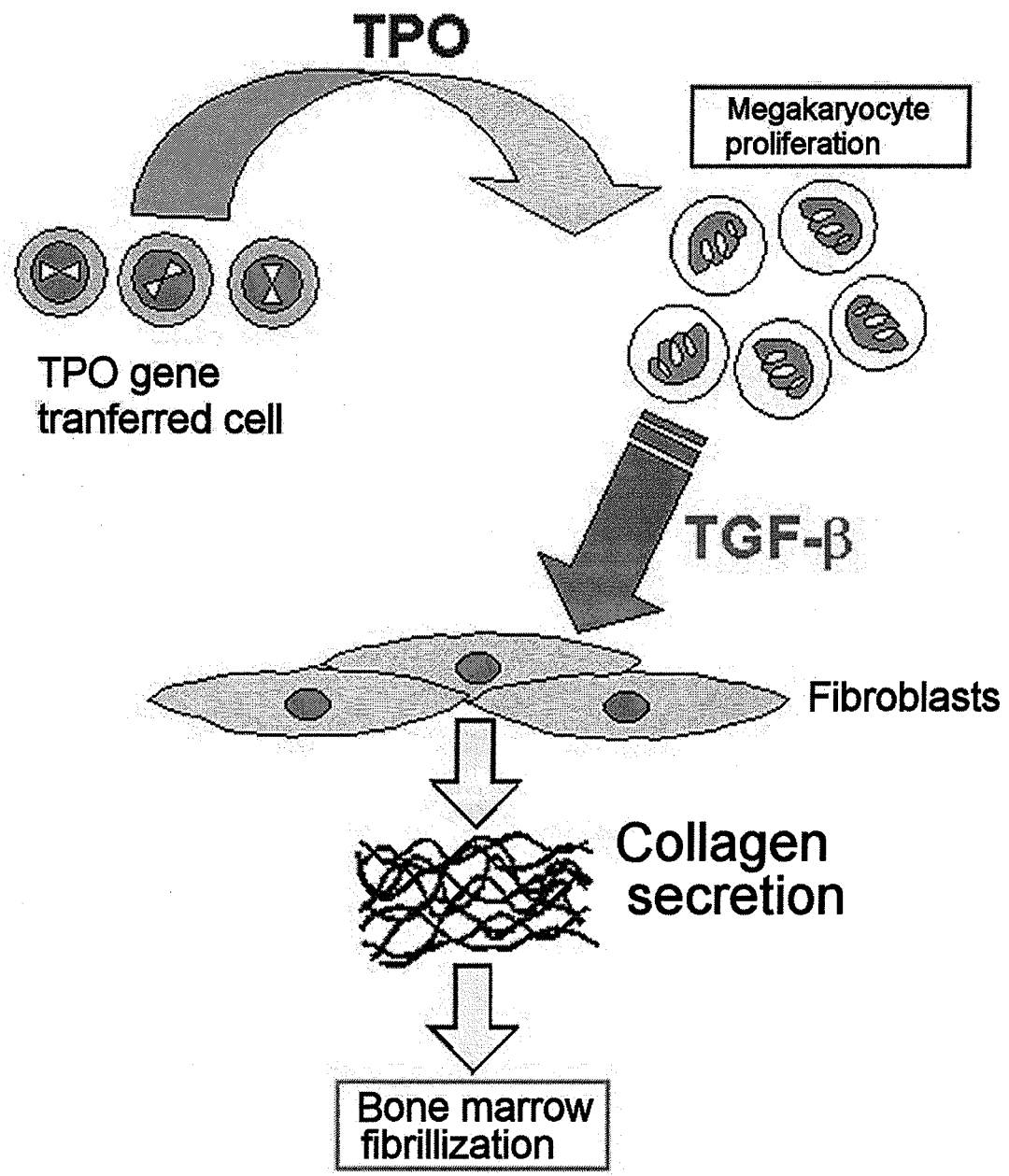
FIG. 2 is a diagram showing the pathogenesis of a myelofibrosis model mouse.

A thrombopoietine (TPO) transgenic mouse developed by Dr. Kazuya Shimoda and Dr. Mine Harada (hereinbelow may also referred to as TPO mouse; see Leukemia Research 29: 761-769, 2005) was used as a myelofibrosis model mouse. In this mouse, TPO is excessively produced from TPO gene-transferred cell, leading to the expansion of megakaryocyte in bone marrow. The expanded megakaryocytes excessively produce transforming growth factor-beta (TGF-β), which stimulates bone marrow fibroblasts, promoting the secretion of collagen from the fibroblasts and resulting in bone marrow fibrillization (see FIG. 2).

Figure 3:
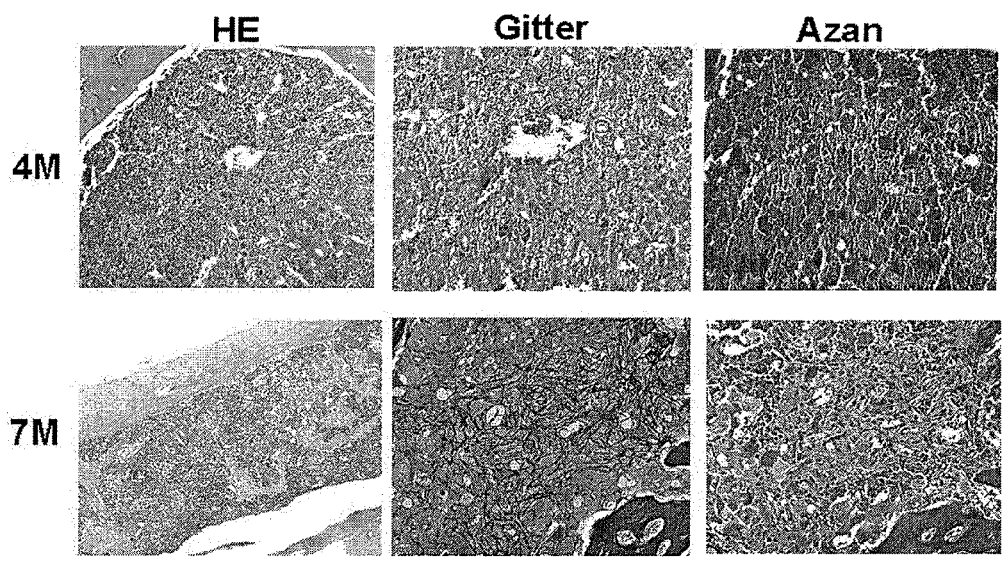
FIG. 3 shows photographs showing bone marrow images of TPO transgenic mice of 4- and 7-months old. The left column shows HE staining images, the central column shows Gitter staining images and the right column shows Azan staining images.
Figure 4:
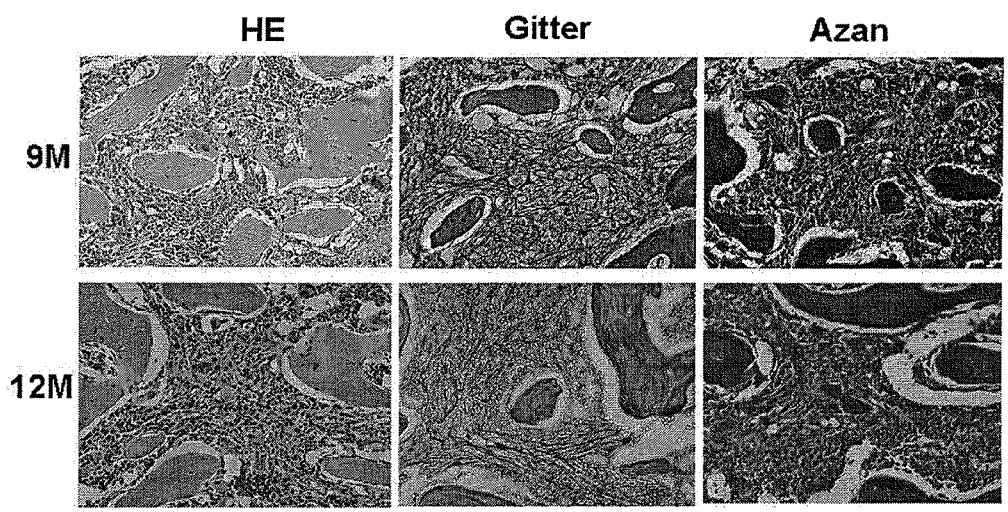
FIG. 4 shows photographs showing bone marrow images of TPO transgenic mice of 9- and 12-months old. The left column shows HE staining images, the central column shows Gitter staining images and the right column shows Azan staining images.

TPO mice (provided from Kyushu University Animal Center) were bred in normal breeding condition, then euthanized at 4, 7, 9 or 12 months after birth, their bone marrow were collected to make tissue samples, which were stained with hematoxylin-eosin (HE) staining, Gitter staining or Azan staining, respectively, and bone marrow images were observed with an optical microscope. The results are shown in FIGS. 3 to 5.

No fibrillization was observed at 4 months old (4M). However, at 7 months old (7M), although trabecular thickening was not apparent (HE), reticular fiber hyperplasia (Gitter) and collagen deposition (Azan) were observed (see FIG. 3).

Both at 9 months old (9M) and 12 months old (12M), trabecular thickening was prominent (HE), reticular fiber hyperplasia (Gitter) and collagen deposition (Azan) were also observed. Moreover, bone marrow fibrillization and trabecular thickening had progressed (exacerbated) at 12M compared with at 9M (see FIG. 4).

Figure 5:
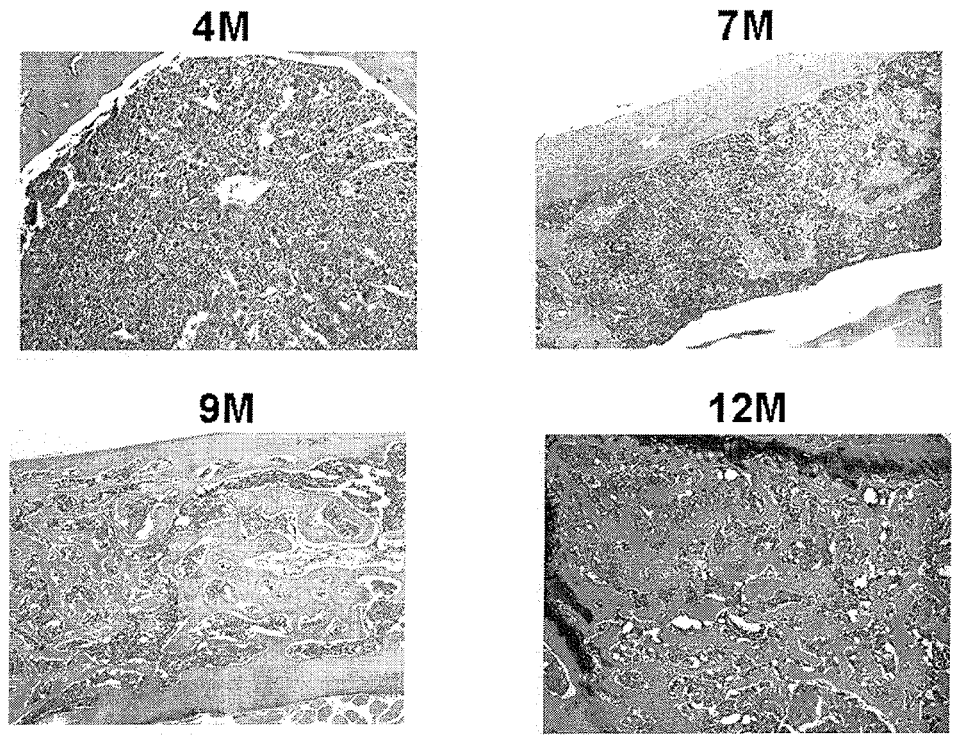
FIG. 5 shows photographs showing the transition in trabecular thickening in TPO transgenic mice. The top left panel is a HE staining image of bone marrow at 4 months old (4M), the top right panel is at 7 months old (7M), bottom left paten is at 9 months old (9M), and the bottom right panel is at 12 months old (12M).

In HE sample of TPO mouse bone marrow, trabecular thickening began at 9 months old (9M), which had further exacerbated at 12 months old (see FIG. 5).

Accordingly, the development of the symptoms of myelofibrosis has been confirmed in TPO mice.

Example 2

Production of siRNAs siRNAs targeted to mouse HSP47 (HSP47 siRNA) were generated as drugs that suppress the activity of extracellular matrix-producing cells in bone marrow. Specifically, five HSP47 siRNAs (HSP47 siRNA-A to E) having the sequences below and a Random siRNA were generated, which were used in the experiments hereinafter. The HSP47 siRNAs were purchased from iGENE Therapeutics, Inc. (Tokyo), and the target sequences of the HSP47 siRNAs were designed from the database Refseq (GenBank Accession No. NM_009825) registered in November 2006. Random siRNA was also purchased from iGENE Therapeutics, Inc. (product name: dsRNA scramble).

```
HSP47 siRNA-A:
                         (sense, SEQ ID NO: 1)
5'-UGGAUGGGAAAGAUGCAGAAGAAGGAG-3'

(antisense, SEQ ID NO: 2)
3'-UAACCUACCCUUUCUACGUCUUCUUCC-5'

HSP47 siRNA-B:
                         (sense, SEQ ID NO: 3)
5'-UGUCUGAGUGGGUAUUUUUAGACAGAG-3'

(antisense, SEQ ID NO: 4)
3'-UAACAGACUCACCCAUAAAAAUCUGUC-5'

HSP47 siRNA-C:
                         (sense, SEQ ID NO: 5)
5'-GAUGCGAGAUGAGUUGUAGAGUCCAAG-3'

(antisense, SEQ ID NO: 6)
3'-UACUACGCUCUACUCAACAUCUCAGGU-5'

HSP47 siRNA-D:
                         (sense, SEQ ID NO: 7)
5'-CAGAACUGCCCAUCCUUAAAAUGAUAG-3'

(antisense, SEQ ID NO: 8)
3'-UAGUCUUGACGGGUAGGAAUUUUACUA-5'

HSP47 siRNA-E:
                         (sense, SEQ ID NO: 9)
5'-GAGACAAGAUGCGAGAUGAGUUGUAAG-3'

(antisense, SEQ ID NO: 10)
3'-UACUCUGUUCUACGCUCUACUCAACAU-5'

Random siRNA:
                         (sense, SEQ ID NO: 11)
5'-CGAUUCGCUAGACCGGCUUCAUUGCAG-3'

(antisense, SEQ ID NO: 12)
3'-UAGCUAAGCGAUCUGGCCGAAGUAACG-5'
``` siRNAs which have been labeled with a fluorescent dye 6'-carboxyfluorescein (6-FAM) at 5' end were also produced.

Example 3

Properties of Primary Cultured TPO Mouse Bone Marrow Fibroblast

Figure 6:
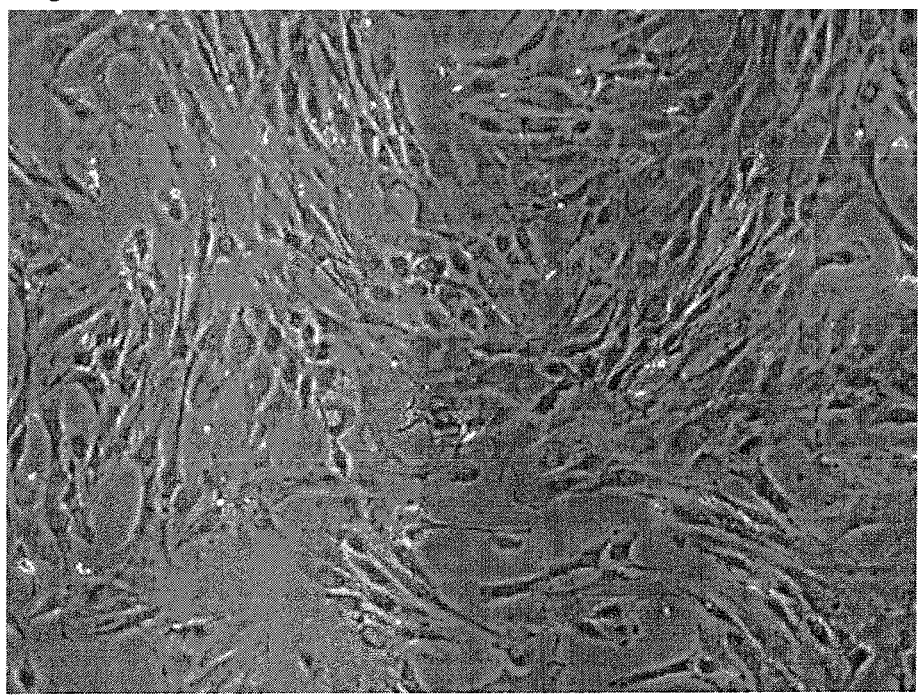
FIG. 6 is a photograph showing cell morphology of TPO mouse-derived primary-cultured bone marrow fibroblasts observed by an inverted microscope (magnification ×400).
Figure 7:
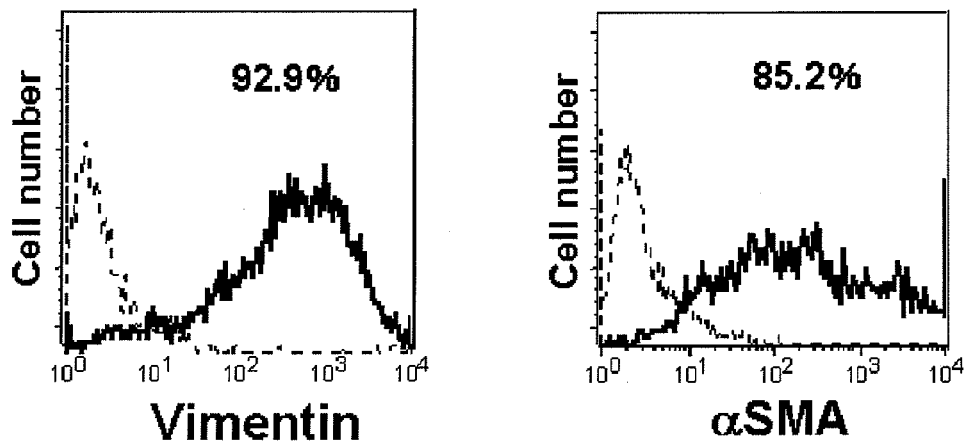
FIG. 7 shows diagrams showing the results of flow cytometric analyses of Vimentin and α-SMA expressions in TPO mouse-derived primary-cultured bone marrow fibroblasts. The vertical axes indicate cell number.

A primary culture of bone marrow fibroblasts was obtained by culturing the bone marrow cells from TPO mice of 4 to 6 weeks old in MEM (Minimum Essential Medium Eagle, Sigma) supplemented with 15% fetal calf serum (FCS) for 4 weeks. FIG. 6 shows the cell morphology observed by an inverted microscope. The cells had a spindle shape which is typical for a fibroblast. FIG. 7 shows the results of flow cytometric analyses using respective antibodies to mesenchymal cell markers Vimentin and α-SMA (anti-Vimentin antibody (Santa Cruz Biotechnology) and anti-α-SMA antibody (Santa Cruz Biotechnology)). The expression of both markers was observed, indicating that the cells obtained from the culture were typical bone marrow fibroblasts. The flow cytometer used in the analyses was FACS calibur (Becton Dickinson), and measured data was analyzed using CellQuest software (Becton Dickinson).

Example 4

Effect of HSP47 siRNA on NIH3T3 Cell (Mouse Fibroblast Cell Line)

$1\times10^5$ NIH3T3 cells were suspended in Dulbecco's modified Eagle's medium (DMEM, Life Technologies) supplemented with 10% Calf serum (CS), and plated onto 6-well culture plates. After 24 hours, NIH3T3 cells at 50-60% confluency were transfected with HSP47 siRNA, using Lipotrust (Hokkaido System Science Co., Ltd.). Specifically, 20 nM Lipotrust and 50 nM Random siRNA or HSP47 siRNA were mixed by a vortex and used for transfection. The transfected NIH3T3 cells were cultured for 4 hours in serum-free OPTI-MEM (GIBCO). The NIH3T3 cells were then washed with DMEM, and further cultured for 24 hours in DMEM supplemented with 10% CS, and protein was extracted. The HSP47 expression was then analyzed by Western blotting. Namely, the protein extracted from the NIH3T3 cells was fractioned using 4/20 SDS-polyacrylamide gel electrophoresis (SDS-PAGE) and then transferred to a nitrocellulose membrane. It is probed firstly either with a primary antibody against HSP47 (Stressgen) or a primary antibody against β-actin (Cell Signaling Technology), then further probed with a peroxidase-conjugated secondary antibody (Oncogene Research Product), and finally developed using ECL (Amersham Life Science).

Figure 8:
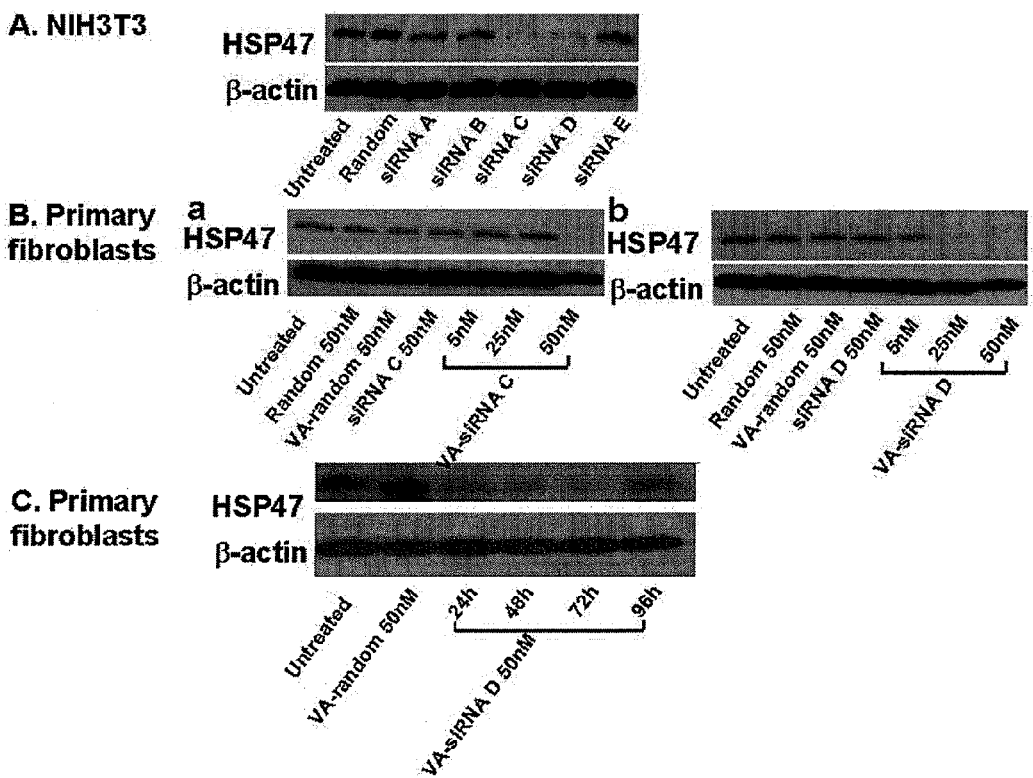
FIG. 8 shows western blot images showing the effect of various siRNA HSP47 on HSP47 expression in NIH3T3 (A) and primary cultures of TPO mouse-derived bone marrow fibroblasts (Primary fibroblasts; B and C).

The result showed that, at 24 hours after the transfer of HSP47 siRNA into NIH3T3 cells, HSP47 siRNA-C and -D had a stronger effect compared to A, B and E (see FIG. 8A). Accordingly, we used HSP47 siRNA-C and -D as HSP47 siRNA in the experiments thereafter.

Example 5

Effect of HSP47 siRNA on TPO Mouse-Derived Primary-Cultured Bone Marrow Fibroblast $5 \times 10^5$ of TPO mouse-derived primary-cultured bone marrow fibroblasts were suspended in MEM supplemented with 15% FCS, and plated onto 6-well culture plates. After 24 hours, bone marrow fibroblasts at 50-60% confluency were transfected with HSP47 siRNA, using Lipotrust. Namely, 20 nM Lipotrust and 50 nM Random siRNA or 5-50 nM HSP47 siRNA-C or -D were mixed by a vortex and used for transfection, or these were further mixed with 40 nM vitamin A (retinol, Sigma) by a vortex, after 5 minutes, and used for transfection. Bone marrow fibroblasts transfected either with vitamin A-conjugated or vitamin A-unconjugated liposome HSP47 siRNA were cultured for 4 hours in serum-free OPTI-MEM. Then these bone marrow fibroblasts were washed with MEM, further cultured for 48 hours in MEM supplemented with 15% FCS, and protein was extracted. In a different experiment, bone marrow fibroblasts transfected with 50 nM vitamin A-conjugated liposome HSP47 siRNA-D (VA-Lip-HSP47 siRNA-D; hereinafter "vitamin A-conjugated" and "liposome" may be abbreviated as "VA" and "Lip", respectively) was cultured for 4 hours in serum-free OPTI-MEM and washed with MEM, then further cultured for 24 to 96 hours in MEM supplemented with 15% FCS before extracting protein. Then extracted protein was analyzed for HSP47 expression by Western blotting. Namely, the protein extracted from the bone marrow fibroblasts was fractioned using 4/20 SDS-polyacrylamide gel electrophoresis (SDS-PAGE) and then transferred onto a nitrocellulose membrane. Then, similar to Example 4, it is probed with a primary antibody against HSP47 or β-actin, then further probed with a peroxidase-conjugated secondary antibody, and finally visualized using ECL. The results are shown in FIGS. 8B and 8C.

When primary cultured bone marrow fibroblasts were used, neither HSP47 siRNA-C (FIG. 8, a) nor HSP47 siRNA-D (FIG. 8, b) alone showed any effect. However, when conjugated with vitamin A (VA), HSP47 siRNA-C (VA-Lip-HSP47 siRNA-C) was confirmed to express an effect in a concentration of at or above 50 nM, while VA-Lip-HSP47 siRNA-D did so at or above than 25 nM. Accordingly, it became clear that it is necessary to use VA-Lip-HSP47 siRNA for an efficient transfer of HSP47 siRNA into a primary cultured bone marrow fibroblast, and that VA-Lip-HSP47 siRNA-D had more potent suppressive effect on HSP47 compared with VA-Lip-HSP47 siRNA-C. Thus, we decided to use VA-Lip-HSP47 siRNA-D in the experiments thereafter.

Furthermore, it became clear that the effect of VA-Lip-HSP47 siRNA-D (50 nM) sustained for 72 hours (see FIG. 8C).

Example 6

Figure 9:
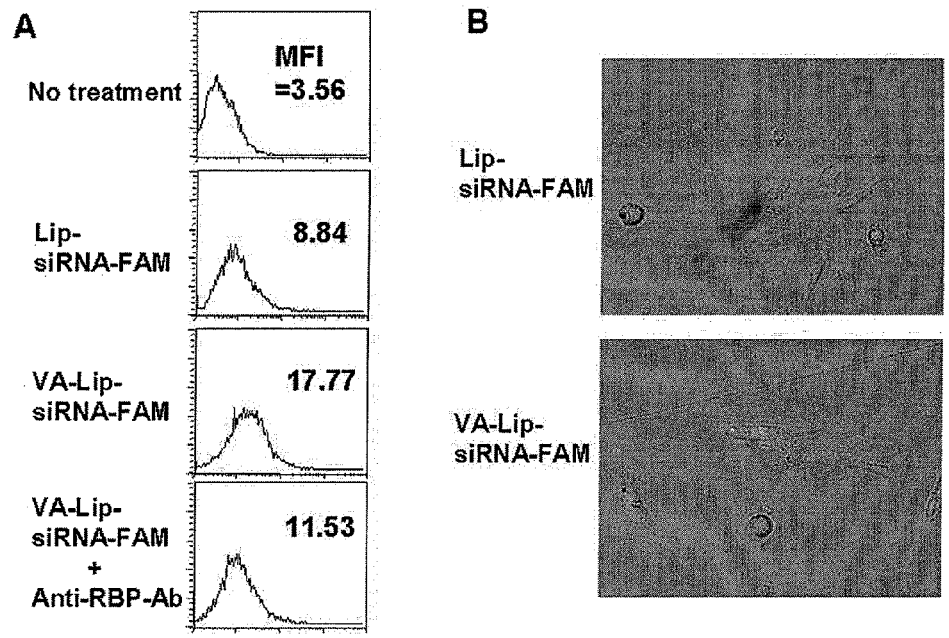
FIG. 9 shows diagrams showing the effect of vitamin A (VA) on the introduction of a liposome-embedded HSP47 siRNA (Lip-siRNA) into TPO mouse-derived primary-cultured bone marrow fibroblasts. (A) and (B) show results of flow cytometric analyses and fluorescence microscopic images, respectively.

Effect of Vitamin A (VA) on the Introduction of Liposome-Embedded HSP47 siRNA (Lip-HSP47 siRNA) in TPO Mouse-Derived Primary-Cultured Bone Marrow Fibroblasts Primary-cultured bone marrow fibroblasts derived from TPO mouse were transfected with Lip-HSP47 siRNA or VA-Lip-HSP47 siRNA conjugated with 50 nM carboxyfluorescein (FAM) (Lip-HSP47 siRNA-FAM or VA-Lip-HSP47 siRNA-FAM) in OPTI-MEM culture medium supplemented with 10% CS, in the presence or absence of 10 mg/ml anti-retinol binding protein antibody (anti-RBP-Ab, BD Pharmingen), and after 30 minutes analyzed by flow cytometry. The mean fluorescence intensity (MFI) of transfected cell was measured by FACS calibur and analyzed using CellQuest software (Becton Dickinson). $5 \times 10^5$ TPO mouse-derived primary-cultured bone marrow fibroblasts were plated onto a 6-well culture plate. After 24 hours, 50 nM VA-Lip-HSP47 siRNA-FAM or Lip-HSP47 siRNA-FAM was added. These cells were cultured for 30 minutes in OPTI-MEM supplemented with 10% FCS, and washed with PBS and fixed with 4% paraformaldehyde thereafter (25 degree C., 15 minutes). Subsequent to fixation, these cells were nuclear-stained with DAPI for 1 minute. The intracellular localization of FAM was evaluated by fluorescence microscope. A typical flow cytometric pattern and a typical result of intracellular localization of FAM-labeled siRNA are shown in FIGS. 9A and 9B, respectively. MFI is as indicated in FIG. 9A. It became clear that, compared with Lip-HSP47 siRNA, VA-Lip-HSP47 siRNA exhibited a higher transfection efficiency into a TPO mouse-derived primary-cultured bone marrow fibroblast (A and B). Furthermore, since the introduction of VA-Lip-HSP47 siRNA was partly suppressed by anti-RBP-Ab (A), it was suggested that a part of VA-Lip-HSP47 siRNA uptake could have been made via RBP (Retinol Binding Protein) receptor of the bone marrow fibroblast.

Example 7

Effect of siRNA HSP47 on Collagen Secretion from TPO Mouse-Derived Primary-Cultured Bone Marrow Fibroblasts $5 \times 10^5$ of primary-cultured bone marrow fibroblasts were suspended in MEM supplemented with 15% FCS, and plated onto 6-well culture plates. After 24 hours, 50 nM of either Lip-siRNA Random (siRNA ran), Lip-HSP47 siRNA-D (siRNA D), VA-Lip-siRNA Random (VA-siRNA ran) or VA-Lip-HSP47 siRNA-D (VA-siRNA D) was introduced. After 4 hours, culture medium was replaced by MEM supplemented with 15% FCS, prior to culturing for another 48 hours. The culture medium was then removed and replaced by serum-free OPTI-MEM, before culturing for another 4 hours. After that, firstly the collagen content in the culture supernatant was measured using Sircol™ Collagen Assay kit (Biocolor). Namely, the culture supernatant was mixed with dye solution for 30 minutes, then the solution was centrifuged at 10,000×g for 10 minutes. After removing unbound dye solution, 1 ml of alkaline reagent was added to the bound dye and vortexed for 10 minutes, and the quantification was made based on the absorbance measured by the absorption spectrometer (540 nm). Secondly, the amount of collagen deposited on the fibroblasts that are attached to the culture plate was quantified by adding Sirius red dye and measuring the absorbance by absorption spectrometer (540 nm).

Figure 10:
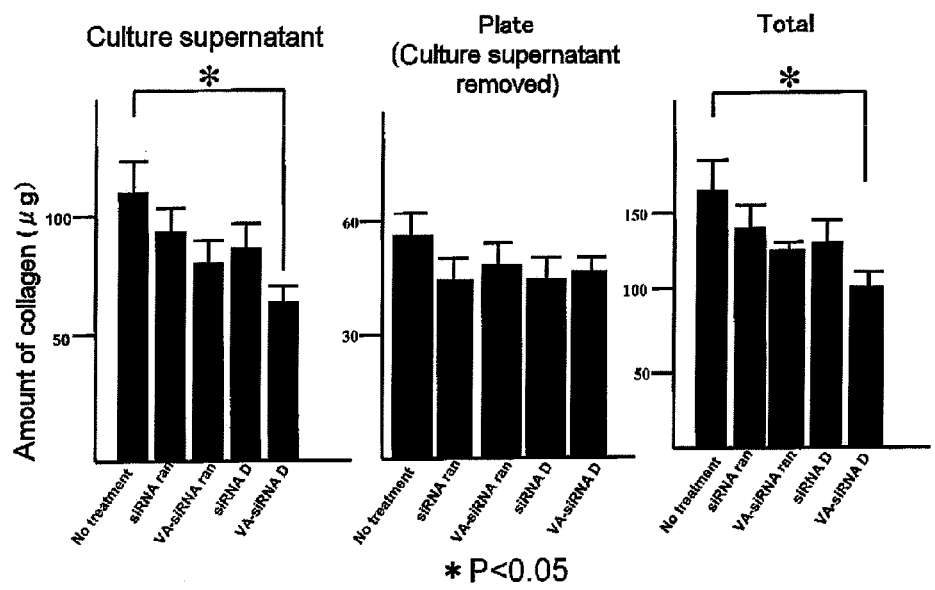
FIG. 10 shows diagrams showing the effect of siRNA HSP47 on collagen secretion by TPO mouse-derived primary-cultured bone marrow fibroblasts.
Figure 11:
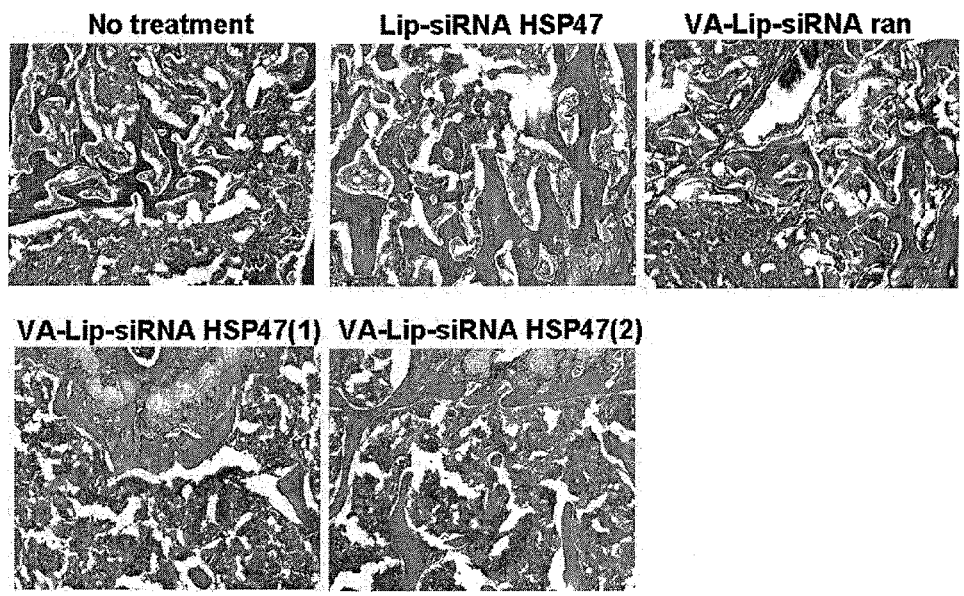
FIG. 11 shows microscopic images of Gitter staining samples showing an in vivo effect of siRNA HSP47 on bone marrow fibrillization in TPO mice.
Figure 12:
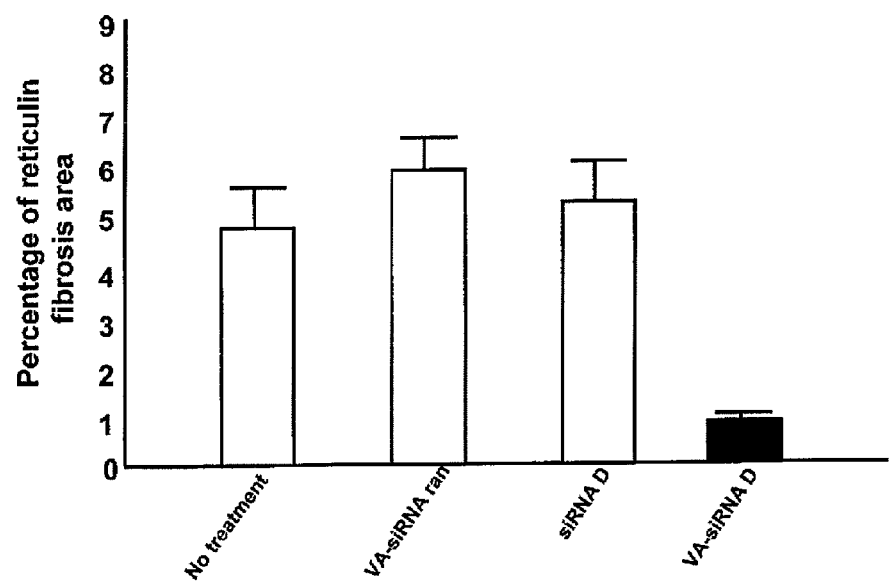
FIG. 12 is a graph showing the quantification of the level of improvement in reticular fiber hyperplasia in TPO mice by siRNA HSP47 by image analyses. The vertical axis indicates the ratio of the dots for reticular fiber against entire dots in each field.

The result is shown in FIG. 10. Note that "Culture Supernatant" in the figure indicates the collagen content in the culture supernatant of the fibroblasts, whereas "Plate (culture supernatant removed)" indicates the amount of collagen deposited on the fibroblasts after removing the culture supernatant, and "Total" indicates the sum of "Culture Supernatant" and "Plate (culture supernatant removed)", respectively. Data was expressed as a mean of 3 cultures±SD (*P<0.05).

As a result, it became clear that the amount of collagen secreted into the culture supernatant from the primary-cultured fibroblasts transfected with VA-Lip-HSP47 siRNA-D was significantly smaller compared to the cases of other cells; that in the cells transfected with VA-Lip-HSP47 siRNA-D, the amount of collagen deposition on the culturing plate was smaller but not significant compared to the cases of other cells; and that, in the fibroblasts transfected with VA-Lip-HSP47 siRNA-D, the sum of the amount of collagen secreted into the culture supernatant from the fibroblasts and the amount of collagen deposition on the fibroblasts after removing the culture supernatant was significantly smaller compared to the cases of other cells.

Example 8

In Vivo Effect of siRNA HSP47 on Bone Marrow Fibrillization of TPO Mice

We investigated the effect of VA-Lip-HSP47 siRNA-D in vivo to improve bone marrow fibrillization using 7-month-old TPO mice. 12.5 mg of HSP47 siRNA-D per mouse was injected intravenously from retro-orbital plexus using tuberculin syringe, every other day to make 4 doses of injection in total. Namely, 12.5 mg/mouse of siRNA (8 µL) and 12.5 nM of Lipotrust (12.5 µL), either with or without 25 nM of vitamin A (2.5 µL), was further topped up with RNAase free PBS to make total 100 µL, which is administered to a mouse as one dose. The mice were euthanized 8 days after the start of HSP47 siRNA-D administration, and the bone marrow was collected for preparing tissue samples, each of which were stained with hematoxylin-eosin (HE) staining, Gitter staining or Azan staining, and subjected to bone marrow image observation by an optical microscope. The results are shown in FIGS. 11-14.

From the Gitter staining sample after treatment (FIG. 11), it became clear that the reticular fiber hyperplasia in bone marrow was significantly improved in the two mice which had been administered VA-Lip-siRNA HSP47 (VA-Lip-siRNA HSP47 (1) and (2)), compared to the untreated mice (No treatment), Lip-siRNA HSP47-administered mice (Lip-siRNA HSP47) and VA-Lip-siRNA Random-administered mice (VA-Lip-siRNA ran). Moreover, the level of this improvement in reticular fiber hyperplasia by siRNA HSP47 was measured and quantified by KS-400 software (Carl Zeiss). Namely, 10 optical fields were selected from a Gitter staining sample after treatment, and the ratio of the dots for reticular fiber against entire dots in each field (percentage of reticulin fibrosis area) was measured as an index of the reticular fiber hyperplasia. It was confirmed that the reticular fiber hyperplasia in bone marrow was significantly improved in the mice which had been administered VA-Lip-siRNA HSP47-D (VA-siRNA D) compared to the untreated mice (No treatment), Lip-siRNA HSP47-administered mice (siRNA D) and VA-Lip-siRNA Random-administered mice (VA-siRNA ran) (see, FIG. 12).

Figure 13:
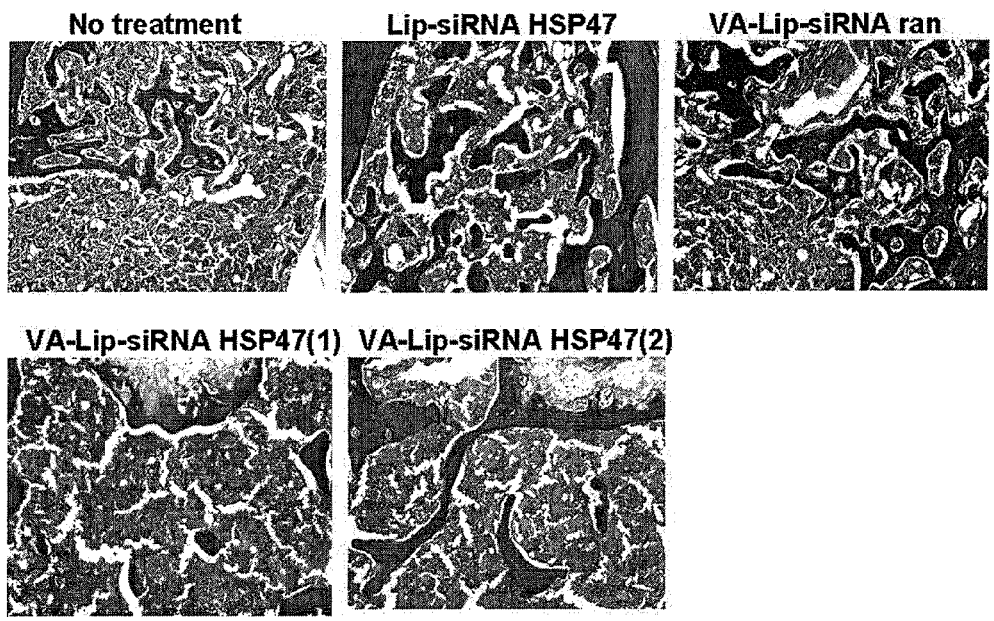
FIG. 13 shows microscopic images of Azan staining samples showing an in vivo effect of siRNA HSP47 on bone marrow fibrillization in TPO mice.

Moreover, from the Azan staining samples after treatment as shown in FIG. 13, it was shown that the collagen hyperplasia in bone marrow was significantly improved in the two mice which had been administered VA-Lip-siRNA HSP47 (VA-Lip-siRNA HSP47 (1) and (2)) compared to the untreated mice (No treatment), Lip-siRNA HSP47-administered mice (Lip-siRNA HSP47) and VA-Lip-siRNA Random-treated mice (VA-Lip-siRNA ran).

Figure 14:
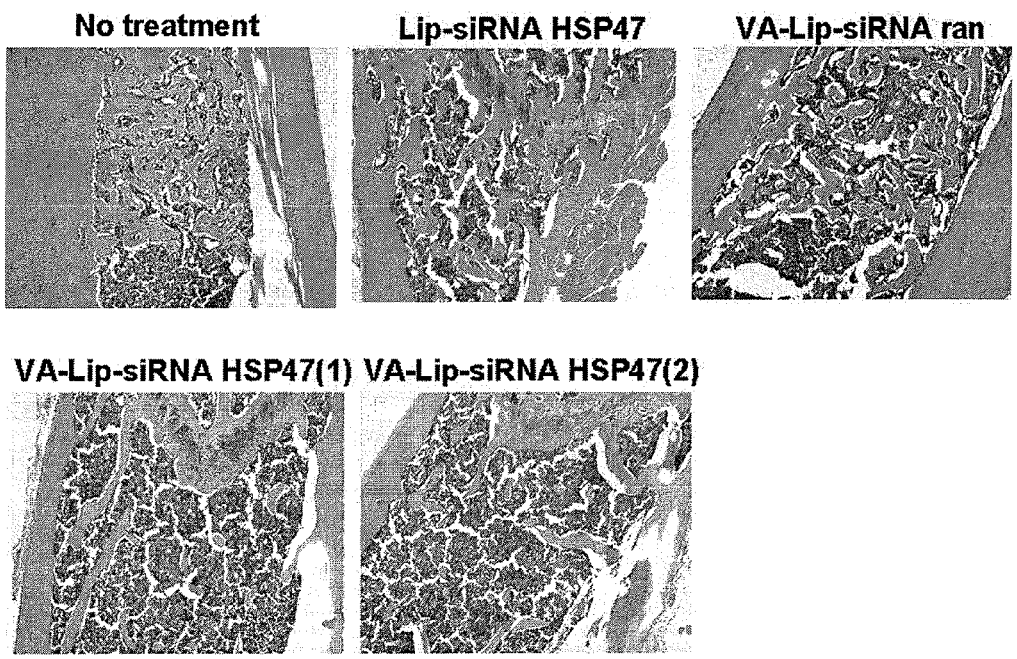
FIG. 14 shows microscopic imaging of HE staining samples showing an in vivo effect of siRNA HSP47 on bone marrow fibrillization in TPO mice.

Furthermore, from the HE staining samples after treatment as shown in FIG. 14, it was shown that the trabecular thickening was significantly improved in the two mice which had been administered VA-Lip-siRNA HSP47 (VA-Lip-siRNA HSP47 (1) and (2)) compared to the untreated mice (No treatment), Lip-siRNA HSP47-administered mice (Lip-siRNA HSP47) and VA-Lip-siRNA Random-administered mice (VA-Lip-siRNA ran).

From these results, it has been suggested that the treatment for myelofibrosis using an siRNA targeted to HSP47 would be useful. Also, in view of the fact that siRNAs basically act in cytoplasm, the results above suggest that a retinoid functioned as a targeting agent to an extracellular matrix-producing cell in bone marrow and efficiently delivered a drug to this cell, and thereby significantly improving the pathology of myelofibrosis.

What is claimed is:

1. A composition for treating myelofibrosis, comprising a carrier that comprises a retinoid and a drug, wherein the carrier is a micelle, a liposome, a microsphere, or a nanosphere, and wherein the drug is (i) an siRNA that reduces the expression of at least one of extracellular matrix constituent molecules selected from the group consisting of collagen, proteoglycan, tenascin, fibronectin, thrombospondin, osteopontin, osteonectin, and elastin, or (ii) an siRNA that reduces the expression of heat shock protein 47, or (iii) a vector that expresses either or both of said siRNAs.

2. The composition according to claim 1, wherein the retinoid comprises retinol.

3. The composition according to claim 1, which is provided in a form that can be prepared immediately before use.

* * * * *

UNITED STATES PATENT AND TRADEMARK OFFICE
CERTIFICATE OF CORRECTION

PATENT NO. : 9,572,886 B2
APPLICATION NO. : 13/921049
DATED : February 21, 2017
INVENTOR(S) : Yoshiro Niitsu It is certified that error appears in the above-identified patent and that said Letters Patent is hereby corrected as shown below:

On the Title Page

In Column 2 (page 3, item (56)) at Line 21, Under Other Publications, change "myelofibrosis and osteoclerosis"" to --myelofibrosis and osteosclerosis"--.

In Column 2 (page 3, item (56)) at Line 36, Under Other Publications, change "(HSC-TS):" to --(HSC-T6):--.

In Column 2 (page 3, item (56)) at Line 62, Under Other Publications, change "lipsomes,"" to --liposomes,"--.

In Column 1 (page 4, item (56)) at Line 9, Under Other Publications, change "compleses,"" to --complexes,"--.

In Column 1 (page 4, item (56)) at Line 17, Under Other Publications, change "Pharmacuetics" to --Pharmaceutics--.

In Column 1 (page 4, item (56)) at Line 24, Under Other Publications, change "theraph:" to --therapy:--.

In Column 1 (page 4, item (56)) at Line 36, Under Other Publications, change ""Imminomicelles:" to --"Immunomicelles:--.

In Column 1 (page 4, item (56)) at Line 39, Under Other Publications, change "soluable" to --soluble--.

In Column 1 (page 4, item (56)) at Line 62, Under Other Publications, change ""Apoptpsis" to --"Apoptosis--.

Signed and Sealed this
Twenty-third Day of May, 2017

Michelle K. Lee
*Director of the United States Patent and Trademark Office*

CERTIFICATE OF CORRECTION (continued)
U.S. Pat. No. 9,572,886 B2

In Column 1 (page 4, item (56)) at Line 69, Under Other Publications, change "receptorg" to --receptor--.

In Column 2 (page 4, item (56)) at Lines 9-10, Under Other Publications, change "complimentary" to --complementary--.

In Column 2 (page 4, item (56)) at Line 25, Under Other Publications, change "oligodeoxpucleotides," to --oligodeoxynucleotides,--.

In Column 2 (page 4, item (56)) at Line 40, Under Other Publications, change ""Nonmenclature" to --"Nomenclature--.

In Column 2 (page 4, item (56)) at Line 68, Under Other Publications, change "ofliposomes," to --of liposomes,--.

In Column 1 (page 5, item (56)) at Line 3, Under Other Publications, change "phosphateyinsulin-" to --phosphate insulin- --.

In Column 1 (page 5, item (56)) at Line 36, Under Other Publications, change "Virolo." to --Virol.--.

In Column 2 (page 5, item (56)) at Line 22, Under Other Publications, change "heptatic metastasis" to --hepatic metastases--.

In Column 2 (page 5, item (56)) at Line 23, Under Other Publications, change "(4-hydroxphenyl" to --(4-hydroxyphenyl)--.

In Column 2 (page 5, item (56)) at Line 32, Under Other Publications, change "ofliposomes" to --of liposomes--.

In the Specification

In Column 5 at Line 9, Change "ideopathic" to --idiopathic--.

In Column 6 at Line 21, Change "acitretine," to --acitretin,--.

In Column 6 at Line 44, Change "acitretine," to --acitretin,--.

In Column 7 at Line 14, Change "dioleylphosphatidylethanolamine" to --dioleoylphosphatidylethanolamine--.

In Column 7 at Line 31, Change "N-α-" to --N-(α- --.

In Column 14 at Line 46, Change "abasic" to --a basic--.

In Column 14 at Line 64, Change "thrombopoietine" to --thrombopoietin--.